US008771668B2

(12) United States Patent
March et al.

(10) Patent No.: US 8,771,668 B2
(45) Date of Patent: Jul. 8, 2014

(54) COMMENSAL BACTERIA AS SIGNAL MEDIATORS WITHIN A MAMMALIAN HOST

(75) Inventors: John C. March, Ithaca, NY (US); Franklin Faping Duan, Ithaca, NY (US)

(73) Assignee: Cornell University, Ithaca, NY (US)

( * ) Notice: Subject to any disclaimer, the term of this patent is extended or adjusted under 35 U.S.C. 154(b) by 378 days.

(21) Appl. No.: 12/937,176

(22) PCT Filed: Apr. 8, 2009

(86) PCT No.: PCT/US2009/039923
§ 371 (c)(1), (2), (4) Date: Mar. 1, 2011

(87) PCT Pub. No.: WO2009/126719
PCT Pub. Date: Oct. 15, 2009

(65) Prior Publication Data
US 2011/0280835 A1    Nov. 17, 2011

Related U.S. Application Data

(60) Provisional application No. 61/043,426, filed on Apr. 9, 2008.

(51) Int. Cl.
| | | |
|---|---|---|
| A01N 63/00 | (2006.01) | |
| C12N 15/74 | (2006.01) | |
| C12N 15/00 | (2006.01) | |
| C07H 21/04 | (2006.01) | |

(52) U.S. Cl.
USPC ........ 424/93.2; 435/320.1; 435/471; 536/23.5

(58) Field of Classification Search
USPC ............... 424/93.2; 435/320.1, 471; 536/23.5
See application file for complete search history.

(56) References Cited

U.S. PATENT DOCUMENTS

| 4,234,570 | A * | 11/1980 | Kanbayashi et al. ......... 514/6.7 |
|---|---|---|---|
| 7,374,930 | B2 | 5/2008 | Oh et al. |
| 2004/0106547 | A1 | 6/2004 | Larsen et al. |
| 2005/0090465 | A1 | 4/2005 | Ferber |
| 2006/0057607 | A1 | 3/2006 | Lenz et al. |
| 2006/0073115 | A1 | 4/2006 | Rivero et al. |
| 2009/0036364 | A1 * | 2/2009 | Levy et al. |
| 2009/0074734 | A1 | 3/2009 | Rottiers |

FOREIGN PATENT DOCUMENTS

| WO | WO 97/29180 | * | 8/1997 |
|---|---|---|---|
| WO | WO/03/046158 | | 6/2003 |

OTHER PUBLICATIONS

Gorecki, D., 2001, Expert Opin. Emerging Drugs, 6(2): 187-198.*
Yla-Herttuala et al., 2000, Lancet, vol. 355, p. 213-222.*
Kodama et al., 2006, Current Medicinal Chemistry, vol. 13, p. 2155-2161.*
Taha, Masoumeh F., 2010, Current Stem Cell research & therapy, vol. 5, p. 23-36.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002 Virology, vol. 304, p. 135-145.*
Chattopadhyay et al., 2004, Virus Research, vol. 99, p. 139-145.*
International Bureau of WIPO, Notification Concerning Transmittal of International Preliminary Report on Patentability and International Preliminary Report on Patentability dated Oct. 21, 2010 (6 pgs.).
International Searching Authority, Korean Intellectual Property Office, International Search Report and Written Opinion issued in corresponding family PCT Application No. PCT/US2009/039923 dated Dec. 31, 2009 (10 pgs.).
Faping, Duan, John C. March, Interrupting *Vibrio cholerae* Infection of Human Epithelial Cells With Engineered Commensal Bacterial Signaling, Biotechnology and Bioengineering, vol. 101, No. 1, pp. 128-134 (Online published Mar. 19, 2008) (7 pgs.).
March, John et al., "Engineering signal transduction for treating type 1 diabetes", 2007 Abstract, Amer. Chem. Society, Div. of Biochemical Technology, BIOT 144 (1 page).
Supplementary European Search Report for EP 09730686.4 dated May 16, 2011 (8 pages).
Steidler L et al "Treatment of Murine Colitis by *Lactococcus lactis* Secreting Interleukin-10," Science, vol. 289, Aug. 25, 2000 (pp. 1352-1355).
Farrar, M.D. et al, "Engineering of the gut commensal bacterium *Bacteroides ovatus* to produce and secrete biologically active murine interleukin-2 in response to xylan," Journal of Applied Microbiology 2005 , vol. 98 (pp. 1191-1197).
Duan F et al, "Secretion of Insulinotropic Proteins by Commensal Bacteria: Rewiring the Gut to Treat Diabetes," Applied and Environmental Microbiology, Dec. 2008, vol. 74, No. 23 (pp. 7437-7438).
Loessner H et al, "Drug-inducible remote control of gene expresson by probiotic *Escherichia coli* Nissle 1917 in intestine, tumor and gall bladder of mice," Microbes and Infection, Dec. 2009, vol. 11, No. 14-15 (pp. 1097-1105).

(Continued)

Primary Examiner — Shin-Lin Chen
(74) Attorney, Agent, or Firm — Pepper Hamilton LLP

(57) ABSTRACT

Genetically engineered cells and microorganisms are provided for preventing or ameliorating diseases through genetically engineered quorum signaling. Therapeutic methods for using the cells and microorganisms to prevent or ameliorate diseases are also provided. The genetically engineered cells or microorganisms can be engineered to express a signal and used to interrupt the signaling-dependent virulence of an invading pathogen. The cells or microorganisms can be used to provide signal-dependent expression of a desirable gene in order to interrupt, prevent, and/or ameliorate a disease of mammals, such as parasitic diseases, infectious diseases, autoimmune diseases and genetic disorders.

8 Claims, 8 Drawing Sheets

(56) References Cited

OTHER PUBLICATIONS

Figure 1:
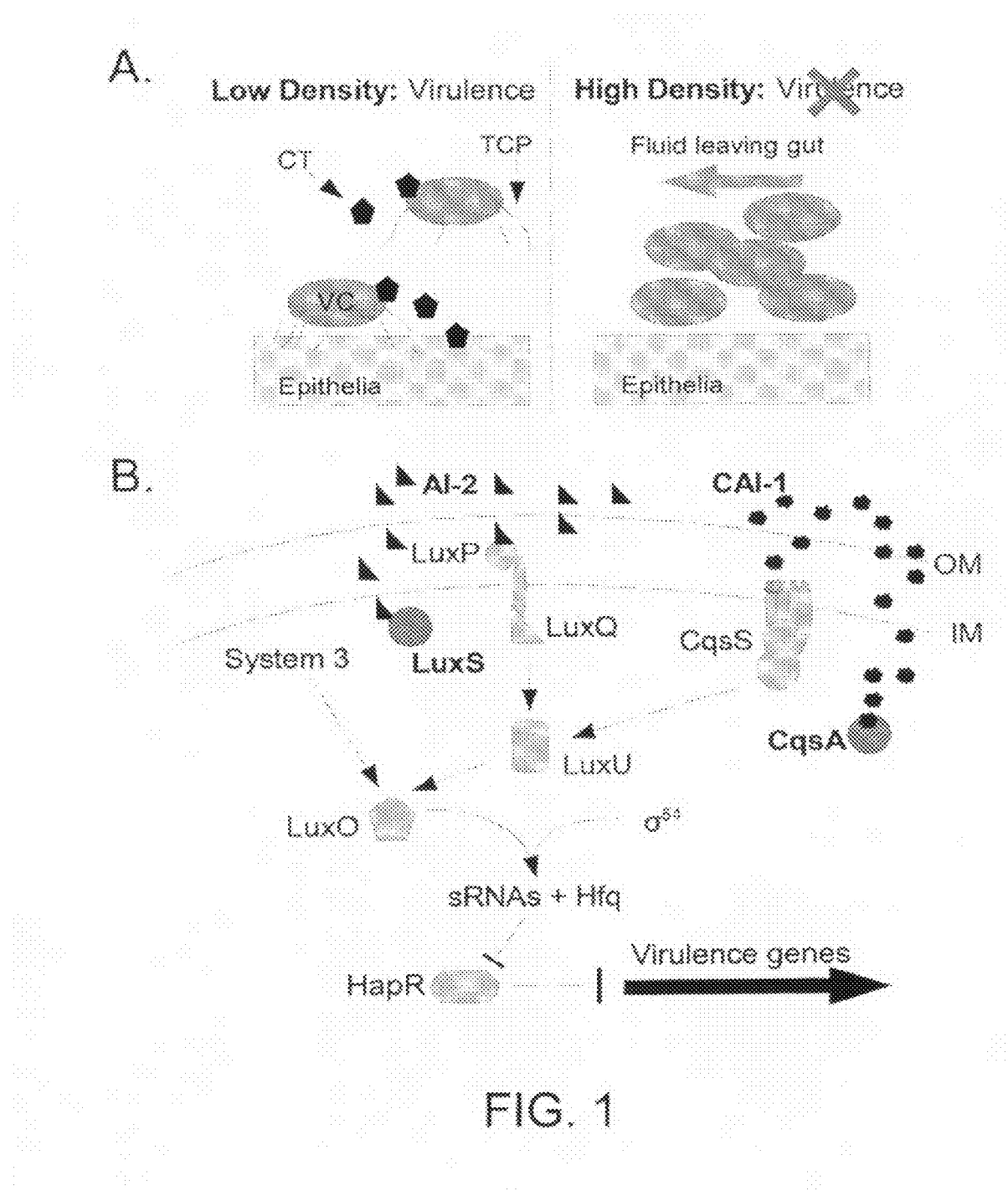

Suzuki A et al, "Glucagon-like peptide 1 (1-37) converts intestinal epithelial cells into insulin-producing cells," Proceedings of the National Academy of Sciences of the United States (PNAS), Apr. 29, 2003, vol. 100, No. 9 (pp. 5034-5039).

Yoshida S et al, "PDX-1 Induces Differentiation of Intestinal Ephithelioid IEC-6 Into Insulin-Producing Cells," Diabetes, Aug. 2002, vol. 51 (pp. 2505-2513).

\* cited by examiner

COMMENSAL BACTERIA AS SIGNAL MEDIATORS WITHIN A MAMMALIAN HOST

CROSS-REFERENCE TO RELATED APPLICATIONS

This application is a national stage application under 35 U.S.C. §371 of PCT Application No. PCT/US2009/039923, filed Apr. 8, 2009, which claims priority to and the benefit of U.S. provisional patent application Ser. No. 61/043,426, filed Apr. 9, 2008, which is incorporated herein by reference in its entirety.

1. TECHNICAL FIELD

The present invention relates genetically engineered microorganisms (e.g., bacteria) having engineered signaling ability, and the use of these engineered microorganisms (or recombinant cells derived therefrom) to stimulate or provide expression of desirable genes in a host organism. The invention also relates to commensal bacteria engineered to express signaling molecules that allow for communication with either the host's cells or with other bacteria either existing within or invading the host.

2. BACKGROUND OF THE INVENTION

Water-borne pathogens kill an estimated 1.7 million people annually and pose a serious threat to both national security in the United States and international economic development (Ashbolt N J. 2004. Microbial contamination of drinking water and disease outcomes in developing regions. Toxicology 198(1-3):229-38; Leclerc H, Schwartzbrod L, Dei-Cas E. 2002. Microbial agents associated with waterborne diseases. Crit Rev Microbiol 28(4):371-409). The enteric disease cholera affects developing nations throughout the world, especially in warmer climates such as Bangladesh (Guerrant R L, Carneiro-Filho B A, Dillingham R A. 2003. Cholera, diarrhea, and oral rehydration therapy: triumph and indictment. Clin Infect Dis 37(3):398-405). Caused by the marine bacterium *Vibrio cholerae*, the disease is marked by diarrhea and severe dehydration. A widely-considered low number for estimated deaths by cholera is between 120,000 and 200,000 deaths annually (Sanchez J, Holmgren J. 2005. Virulence factors, pathogenesis and vaccine protection in cholera and ETEC diarrhea. Current Opinion in Immunology 17(4):388-398). Defense against this and other enteric diseases is hampered by their large scale, relative poverty of the outbreak areas, and lack of specificity in the treatment options: that is, when broadband antimicrobials are used to fight *V. cholerae* infection, it opens up the intestinal tract for colonization by opportunistic pathogens such as *Clostridium difficile*.

The intestinal tract is home to at least 395 phylotypes of bacteria (Eckburg P B, Bik E M, Bernstein C N, Purdom E, Dethlefsen L, Sargent M, Gill S R, Nelson K E, Relman D A. 2005. Diversity of the human intestinal microbial flora. Science 308(5728):1635-8). These commensal bacteria (probiotics) have co-evolved with their host to provide nutrients, protect against pathogens, and aid in intestinal development (Holzapfel W H, Haberer P, Snel J, Schillinger U, Huis in't Veld J H. 1998. Overview of gut flora and probiotics. Int J Food Microbiol 41(2):85-101). Both pathogenic and non-pathogenic bacteria in the gut are known to use density-dependent cell to cell signaling (quorum sensing) to coordinate their growth and virulence (Kaper J B, Sperandio V. 2005. Bacterial cell-to-cell signaling in the gastrointestinal tract. Infect Immun 73(6):3197-209). For this reason quorum sensing has emerged as having tremendous potential for aiding in the control of pathogenic growth in the gut and elsewhere. Although there has been some success with using quorum sensing against pathogenic bacteria (March J C, Bentley W E. 2004. Quorum sensing and bacterial cross-talk in biotechnology. Curr Opin Biotechnol 15(5):495-502; Xavier K B, Bassler B L. 2005. Interference with AI-2-mediated bacterial cell-cell communication. Nature 437(7059): 750-3), the full potential of this approach has been hampered by a lack of knowledge about the function of quorum sensing and about ways to exploit what knowledge exists. There have also been successful attempts to use commensal bacteria in preventing cholera disease symptoms through non-quorum-related mechanisms (Focareta A, Paton J C, Morona R, Cook J. Paton A W. 2006. A recombinant probiotic for treatment and prevention of cholera. Gastroenterology 130(6):1688-95). However, no one has yet to demonstrate the successful use of cell-to-cell signaling in preventing an invading pathogen from exhibiting virulence.

*V. cholerae* uses quorum sensing to coordinate its infection of the human GI tract (Miller M B, Skorupski K, Lenz D H, Taylor R K, Bassler B L. 2002. Parallel quorum sensing systems converge to regulate virulence in *Vibrio cholerae*. Cell 110(3):303-14). When at a low cell density, *V. cholerae* expresses virulence factors toxin-coregulated pilus (TCP) and cholera toxin (CT). TCP allows the invading *V. cholerae* to attach to the inside of the GI tract (Taylor R K, Miller V I, Furlong D B, Mekalanos J J. 1987. Use of phoA gene fusions to identify a pilus colonization factor coordinately regulated with cholera toxin. Proc Natl Acad Sci USA 84(9):2833-7) and CT triggers diarrhea and dehydration by stimulating adenylate cyclase (Moss J, Vaughan M. 1979. Activation of adenylate cyclase by choleragen. Annu Rev Biochem 48:581-600) (FIG. 1B). At higher cell densities, TCP and CT expression abates and expression of proteases that degrade the attachment matrix commences through a quorum-regulated circuit (Zhu J, Miller M B, Vance R E, Dziejman M, Bassler B L, Mekalanos J J. 2002. Quorum-sensing regulators control virulence gene expression in *Vibrio cholerae*. Proc Natl Acad Sci USA 99(5):3129-34).

While the purpose of this mechanism is not fully understood, it has been proposed that having virulence so timed allows for detachment and either relocation within or emergence from the human host once a high population density has been reached (Zhu J, Miller M B, Vance R E, Dziejman M, Bassler B L, Mekalanos J J. 2002. Quorum-sensing regulators control virulence gene expression in *Vibrio cholerae*. Proc Natl Acad Sci USA 99(5):3129-34) (FIG. 1A).

FIG. 1 shows a schematic of *V. cholerae*'s infection cycle and quorum sensing circuit. At low cell density in the gut (FIG. 1A), *V. cholerae* (VC, ovals) expresses virulence factors cholera toxin (CT, pentagons) and toxin co-regulated pilus (TCP, strands), which infect the host epithelial cells (epithelia, rectangles) and allow VC to attach to the epithelia, respectively. At high cell density in the gut, VC stop expressing virulence genes and can therefore detach and leave the host with the efflux of fluid.

Two autoinducing molecules have been linked to quorum-related gene control in *V. cholerae*, cholera auto-inducer 1 (CAI-1) and auto-inducer 2 (AI-2). FIG. 1B shows the quorum network of *V. cholerae*: CqsA produces the autoinducer signal CAI-1 and LuxS produces the autoinducer signal AI-2. These systems converge with System 3 at Lux O to down-regulate virulence gene expression at high densities. High cell densities result in accumulation of CAI-1 and AI-2 to convert the signal cascade from kinase to phosphatase activity, repressing the transcription of sRNAs responsible for allowing virulence. (OM=outer membrane, IM=inner membrane).

There is a third component to the quorum regulatory circuit in *V. cholerae* (System 3), but this has been shown to act internally, without an external signal (Miller M B, Skorupski K, Lenz D H, Taylor R K, Bassler B L. 2002. Parallel quorum sensing systems converge to regulate virulence in *Vibrio cholerae* (Cell 110(3):303-14)). CAI-1 is encoded by the gene cqsA in *V. cholerae* and AI-2 is encoded by the gene luxS.

*V. cholerae* El Tor serotypes are largely responsible for outbreaks of cholera in the developing world. The infection cycle for some strains of *V. cholerae* is coordinated, at least in part, through quorum sensing. That is, the expression of virulence genes depends on the concentration of *V. cholerae* autoinducers cholera autoinducer 1 (CAI-1) and autoinducer 2 (AI-2). High concentrations of CAI-1 and AI-2 have been shown previously to inhibit virulence gene expression.

There is therefore a need in the art for methods for using cell-to-cell signaling to prevent an invading pathogen from exhibiting virulence. There is also need in the art for recombinant microorganisms that are engineered to express signaling molecules that allow for communication with either the host's cells or with other bacteria either existing within or invading the host.

Citation or identification of any reference in Section 2, or in any other section of this application, shall not be considered an admission that such reference is available as prior art to the present invention.

3. SUMMARY OF THE INVENTION

The invention provides commensal bacteria and isolated recombinant cells derived therefrom that are engineered to express signaling molecules that allow for communication with either the host's cells or with other bacteria either existing within or invading the host.

In one embodiment, the invention provides an isolated recombinant cell comprising a recombinant nucleic acid encoding a signal, wherein:

the cell is derived from a first organism that is a microorganism, the signal is capable of being expressed by the cell, and the signal regulates signal-dependent expression of a target nucleic acid.

In another embodiment, the signal is secreted by the cell and secretion by the cell is controlled by an environmental stimulus. In another embodiment, the signal stimulates or inhibits expression of the target nucleic acid.

In another embodiment, the environmental stimulus is secreted by a pathogen, or the presence of the environmental stimulus is indicative of the pathogen.

In another embodiment, the pathogen is an invading pathogen and the signal inhibits or disrupts the pathogenicity or virulence of the invading pathogen.

In another embodiment, the target nucleic acid controls pathogenesis or virulence of a pathogen. In another embodiment, the target nucleic acid encodes a virulence factor of an invading pathogen.

In another embodiment, the target nucleic acid is expressed by a mammal. In another embodiment, the target nucleic acid encodes a mammalian factor. The mammalian factor can, for example, promote normal functioning of a physiological process in a mammalian subject or is effective in preventing onset, establishment, or spread of a non-infectious disease within the mammalian subject.

In another embodiment, the target nucleic acid encodes a disease-causal factor associated with onset of a mammalian non-infectious disease.

In another embodiment, the microorganism is a bacterium. The bacterium can be, for example, an enteric bacterium or a commensal bacterium. In one embodiment, the commensal bacterium is a strain of an *Escherichia coli* bacterium. In a specific embodiment, the strain of *Escherichia coli* is *Escherichia coli* Nissle 1917.

In another embodiment, the signal prevents, detects, ameliorates or treats a disease or disorder in a human or animal. The animal can be, for example, in the phylum Chordata, e.g., a mammal or human, or an insect, to name but a few.

In another embodiment, the signal stimulates expression of the target nucleic acid. In another embodiment, the signal comprises a quorum signal.

In another embodiment, the invading pathogen is a protozoan, a pathogenic bacterium, a fungus or a virus. In a specific embodiment, the invading pathogen is *Vibrio cholerae*.

In another embodiment, the signal comprises an antimicrobial peptide or molecule.

In another embodiment, the signal is expressed constitutively by the cell.

In another embodiment, the expression of the recombinant nucleic acid encoding the signal is under the control of an inducible promoter.

In another embodiment, the recombinant cell further comprises a recombinant nucleic acid encoding a recombinant response molecule, wherein the recombinant response molecule detects a molecule present in a host.

In another embodiment, the disease is diabetes. According to this embodiment, the signal can comprise Glp-1, PDX-1, or GIP. The environmental stimulus can be glucose or a sugar that stimulates insulin release within a healthy human.

In a specific embodiment, the signal comprises *Vibrio cholerae* cholera autoinducer 1 (CAI-1) quorum signal, the recombinant nucleic acid encoding the signal comprises a *Vibrio cholerae* cqsA gene encoding CAI-1, the target nucleic acid is *Vibrio cholerae* cholera toxin (CT), and expression of CAI-1 inhibits expression of CT by *Vibrio cholerae*.

In another specific embodiment, the signal comprises *Vibrio cholerae* cholera autoinducer 2 (AI-2) quorum signal, the recombinant nucleic acid encoding the signal comprises a *Vibrio cholerae* luxS gene encoding AI-2, the target nucleic acid is *Vibrio cholerae* toxin-coregulated pilus (TCP), and expression of AI-2 inhibits expression of TCP by *Vibrio cholerae*.

In another specific embodiment, the signal comprises a mammalian insulin secretion-stimulating peptide, the signal regulates expression of insulin in mammalian insulin-secreting cells, and expression of the signal by the cell stimulates glucose-responsive insulin production in a host mammalian subject, e.g., a human. According to this embodiment, the recombinant cell can also comprise an recombinant nucleic acid encoding a recombinant response molecule, wherein the recombinant response molecule detects a molecule present in the host mammalian subject. The mammalian insulin secretion-stimulating peptide can be, e.g., glucagon-like peptide 1 (GLP-1) or pancreatic and duodenal homeobox gene 1 (PDX-1). The mammalian insulin-secreting cells can be intestinal epithelial cells.

A method for regulating expression of a target nucleic acid in a host subject is also provided. The method comprises providing an isolated recombinant cell of the invention (or a microorganism comprising or consisting of the cell of the invention) and administering the cell (or the microorganism comprising or consisting of the cell) to the host subject under conditions effective to allow the signal to be expressed in the host subject, thereby regulating signal-dependent expression of the target nucleic acid in the host subject.

In one embodiment, the signal prevents, detects, ameliorates or treats a disease or disorder in a human or animal or cell derived therefrom. In another embodiment, the signal stimulates expression of the target nucleic acid. In a specific embodiment, the signal comprises a quorum signal. In another embodiment, the signal comprises an antimicrobial peptide or molecule.

The target nucleic acid can encode a virulence factor of the invading pathogen. The invading pathogen can be, e.g., a protozoan, a pathogenic bacterium, a fungus or a virus. In a specific embodiment, the invading pathogen is *Vibrio cholerae.*

In a specific embodiment of the method, the signal comprises *Vibrio cholerae* cholera autoinducer 1 (CAI-1) quorum signal, the recombinant nucleic acid encoding the signal comprises a *Vibrio cholerae* cqsA gene encoding CAI-1, the target nucleic acid is *Vibrio cholerae* cholera toxin (CT), and expression of CAI-1 inhibits expression of CT by *Vibrio cholerae.*

In another specific embodiment, the signal comprises *Vibrio cholerae* cholera autoinducer 2 (AI-2) quorum signal, the recombinant nucleic acid encoding the signal comprises a *Vibrio cholerae* luxS gene encoding AI-2, the target nucleic acid is *Vibrio cholerae* toxin-coregulated pilus (TCP), and expression of AI-2 inhibits expression of TCP by *Vibrio cholerae.*

In another specific embodiment, the signal comprises a mammalian insulin secretion-stimulating peptide, the signal regulates expression of insulin in mammalian insulin-secreting cells, and expression of the signal by the cell stimulates glucose-responsive insulin production in a host mammalian subject.

In another embodiment, the recombinant cell comprises a recombinant nucleic acid encoding a recombinant response molecule, wherein the recombinant response molecule detects a molecule present in the host mammalian subject, e.g., a human. In one embodiment, the mammalian insulin-secreting cells are intestinal epithelial cells.

In one embodiment, the mammalian insulin secretion-stimulating peptide is glucagon-like peptide 1 (GLP-1) that stimulates glucose-responsive insulin production in a mammalian subject.

In another embodiment, the mammalian insulin secretion-stimulating peptide is pancreatic and duodenal homeobox gene 1 (PDX-1) that stimulates constitutive insulin production in a mammalian subject.

In another embodiment, the mammalian insulin secretion-stimulating peptide is GIP peptide that stimulates glucose-responsive insulin production in a mammalian subject.

A method for preventing or ameliorating an infectious or non-infectious disease in a mammalian subject is also provided. The method comprises providing an isolated recombinant cell of the invention (or a microorganism comprising or consisting of the cell of the invention); and administering the cell (or a microorganism comprising or consisting of the cell) to the mammalian subject under conditions effective to stimulates expression of the disease-preventing factor or inhibits expression of the causal factor of the disease, thereby preventing or ameliorating the disease.

In one embodiment, the non-infectious disease is an autoimmune disease, e.g., Type 1 diabetes.

In a specific embodiment, the signal comprises PDX-1, the disease-preventing factor is insulin, and PDX-1 stimulates constitutive production of insulin in the mammalian subject.

In another specific embodiment, the signal comprises Glp-1, the disease-preventing factor is insulin, and Glp-1 stimulates glucose-responsive insulin in the mammalian subject. In another specific embodiment, the signal comprises GIP, the disease-preventing factor is insulin, and GIP stimulates glucose-responsive insulin in the mammalian subject.

In another embodiment, the invention provides the use of an effective material selected from the group consisting of a signal, a fragment thereof, a complex thereof, a derivative thereof, an analog thereof, an expressible nucleic acid coding for the effective material or a fragment or derivative thereof, wherein the signal regulates expression of a target nucleic acid; and a non-pathogenic microorganism comprising the nucleic acid and capable of expressing the signal, for the treatment of a disease or disorder of a human or animal subject.

In one embodiment, the signal inhibits or disrupts the pathogenicity or virulence of an invading pathogen. In another embodiment, the signal prevents, detects, ameliorates or treats the disease or disorder in a human or animal subject.

In another embodiment, the disease is an infectious disease or non-infectious disease.

In another embodiment, the treatment takes place by the administration of isolated and purified effective material in a pharmaceutical composition.

In another embodiment, the effective material is administered in a dose which is sufficient to heal the disease state or to prevent it, to stop the progression of the disease or to alleviate symptoms of the disease.

In another embodiment, the effective material is administered orally, rectally, parenterally, by injection, by infusion or by spray or inhaler to the subject.

In another embodiment, the non-pathogenic microorganism is capable of producing the effective material before, during or after administration to the human or animal subject and to release the produced effective material after administration to cells or tissues of the subject.

In another embodiment, the non-pathogenic microorganism is a commensal bacterium or fungus of humans or animals.

In another embodiment, the non-pathogenic microorganism belongs to the natural intestinal flora of humans or animals.

In another embodiment, the non-pathogenic microorganism is an aerobic or anaerobic gram-negative bacterium of the intestinal flora.

In another embodiment, the gram-negative bacterium belongs to the genus *Escherichia, Pseudomonas, Bacteroides, Lactobacillus. Lactococcus, Bacillus*, or *Proteus.*

In another embodiment, the gram-negative bacterium is *Escherichia coli* (Nissle 1917).

In another embodiment, non-pathogenic microorganism is an aerobic or anaerobic gram-positive or gram negative bacterium of the intestinal flora.

In another embodiment, the gram-positive bacterium belongs to the genus *Bifidobacterium, Streptococcus, Staphylococcus*, or *Corynebacterium.*

In another embodiment, the nucleic acid coding for the signal or a fragment or derivative thereof is inserted into a vector.

In another embodiment, the vector is a plasmid, cosmid, bacteriophage or virus.

In another embodiment, the nucleic acid inserted into the vector is under the functional control of at least one regulating element that ensures the transcription of the nucleic acid in a translatable RNA or the translation of the RNA into a protein, before, during or after the administration. In another embodiment, the at least one regulating element is a promoter, a ribosome binding site, a signal sequence or a 3'-transcription terminator.

In another embodiment, the promoter is an inducible promoter. In a specific embodiment, the inducible promoter is induced by a signaling cascade comprising at least one element in response to an environmental stimulus or stimuli.

In another embodiment, the signal sequence is a bacterial or fungal signal sequence that effects the secretion of the protein out of the cytoplasm of the microorganism into the periplasmic space or into the environment of the microorganism.

In another embodiment, the non-pathogenic microorganism is contained in a pharmaceutical or food composition.

In another embodiment, the effective material is administered orally, rectally, parenterally, by injection, by infusion or by spray or inhaler to the subject.

A pharmaceutical or food composition is provided. The composition can comprise at least one cell of a non-pathogenic microorganism capable of producing the effective material and containing an expressible nucleic acid encoding a signal or a fragment or derivative thereof. In one embodiment, the microorganism is an anaerobic or aerobic, gram-negative or gram-positive, bacterium of the intestinal flora. In another embodiment, the microorganism is a commensal bacterium of humans or animals.

In another embodiment, the nucleic acid coding for the signal or a fragment or derivative thereof is inserted into an expression vector, and wherein the expression of the nucleic acid is under the control of at least one regulating element, so that the effective material is expressed before, during or after the administration of the pharmaceutical or food composition, and is released to cells or tissues of a human or animal host after the administration of the pharmaceutical or food composition.

A method for producing a pharmaceutical or food composition is also provided. The method comprises:

(a) isolating or synthesizing a nucleic acid coding for an effective material, wherein the effective material is selected from the group consisting of a signal, a fragment thereof, a complex thereof, a derivative thereof, an analog thereof, an expressible nucleic acid coding for the effective material or a fragment or derivative thereof;

(b) cloning the nucleic acid coding for the signal in a microbial expression vector;

(c) transforming the recombinant expression vector obtained in (b) in a microbial host cell, where the microbial host cell is a commensal of a human or animal host;

(d) propagating the transformed microbial host cells;

(e) producing an immobilized, lyophilized, liquid preparation or suspension of transformed microbial host cells; and (f) mixing the immobilized, lyophilized, liquid preparation or suspension of transformed microbial host cells obtained in (e) with physiologically acceptable excipients, stabilizers, thickeners, parting agents, lubricants, emulsifiers or the like materials to obtain a pharmaceutical or food composition.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. Schematic of *V. cholerae*'s infection cycle and quorum sensing circuit. See Section 6.1 for details.

Figure 2:
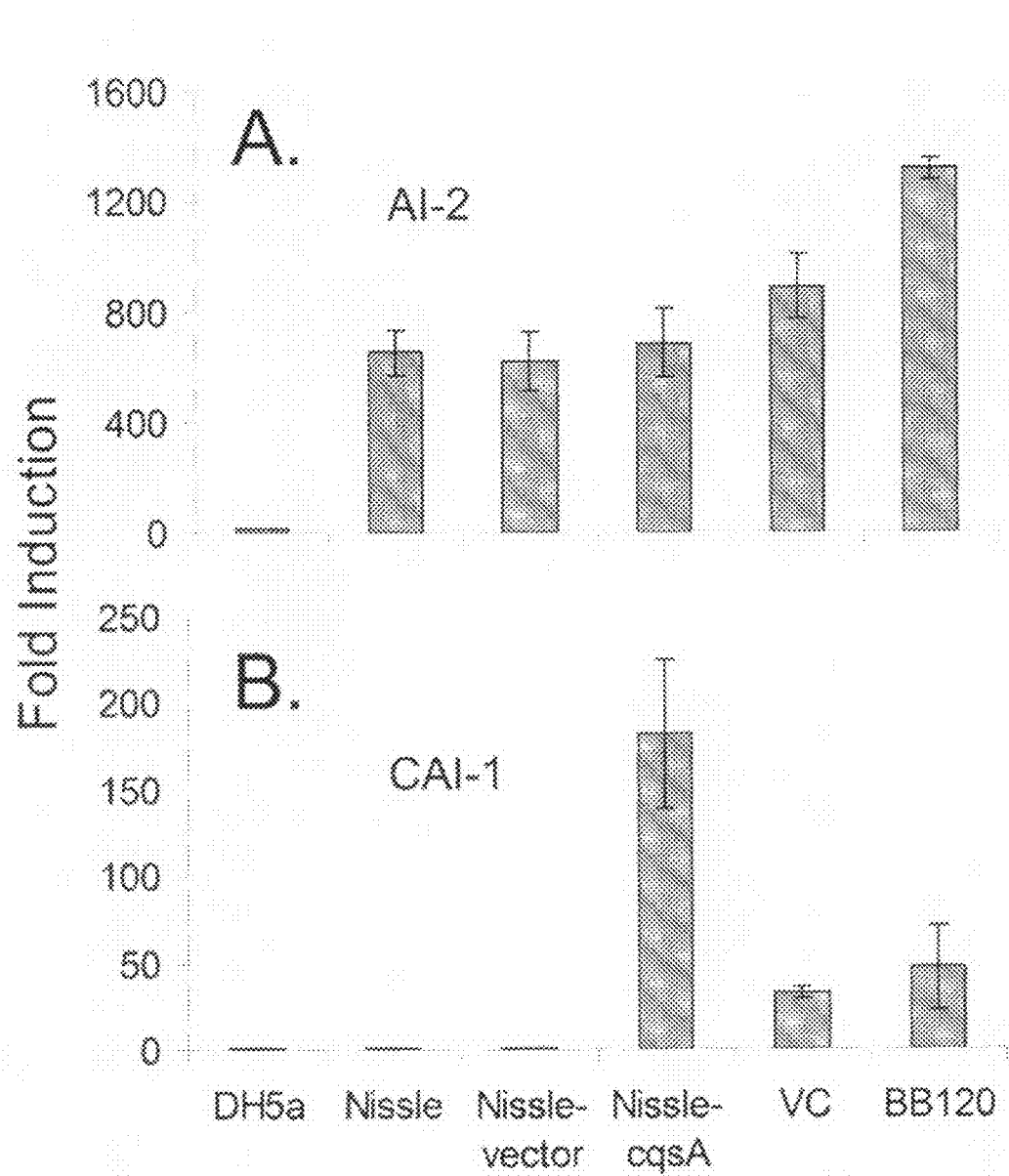

FIG. 2. Expression of autoinducers in engineered commensal bacteria. See Section 6.1 for details.

Figure 3:
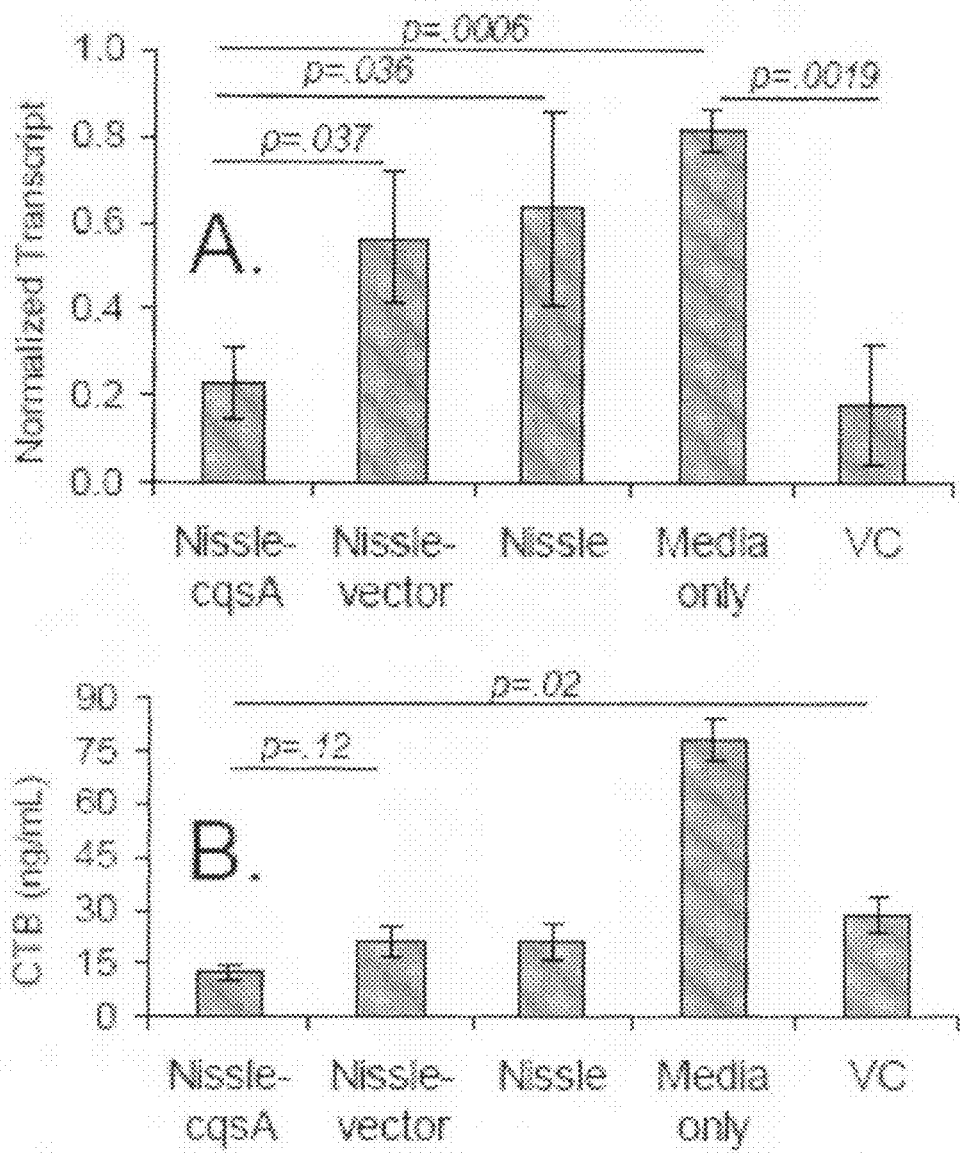

FIG. 3. Interruption of *V. cholerae* virulence in culture media. See Section 6.1 for details.

Figure 4:
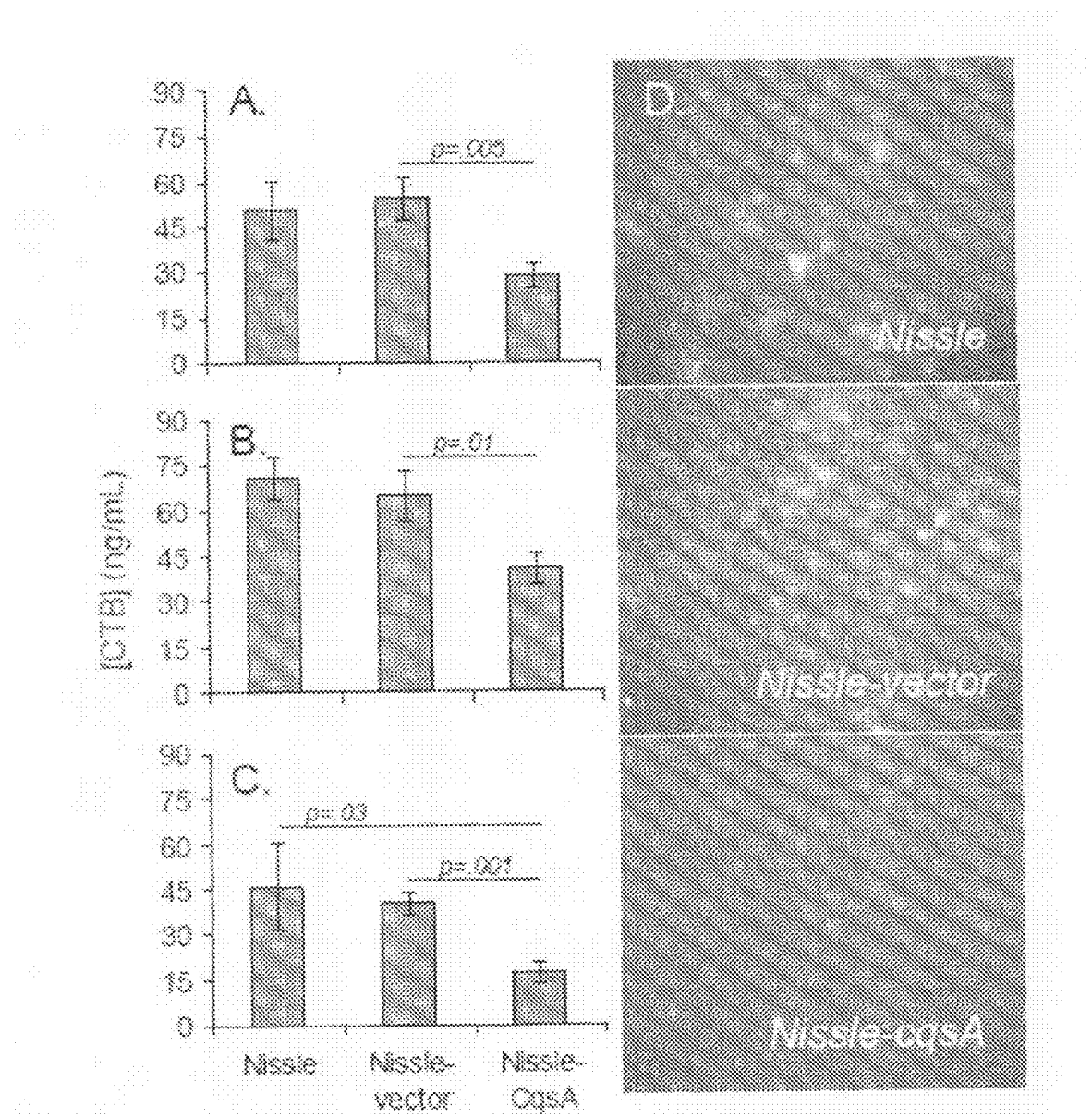

FIG. 4. Interruption of *V. cholerae* virulence in co-cultures. See Section 6.1 for details.

Figure 5:
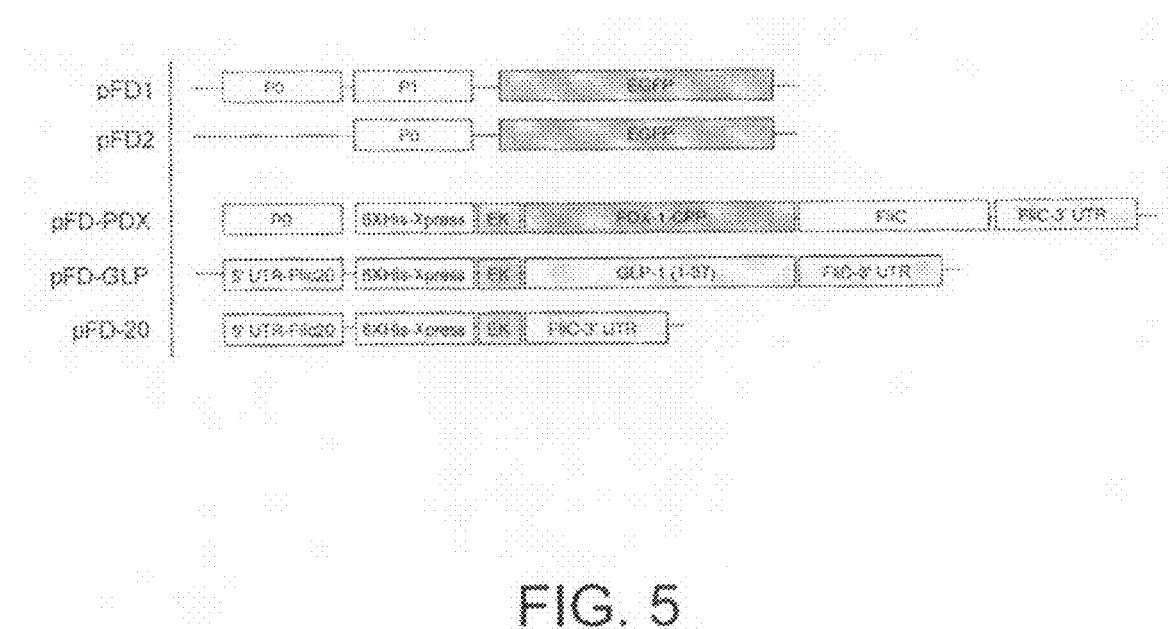

FIG. 5. Plasmids made for study described in Section 6.2. To study the P0/P1 promoters from *E. coli* DH5α two plasmids were made (pFD1 and pFD2). pFD1 encoded the entire P0/P1 region to drive the expression of enhanced green fluorescent protein (EGFP). pFD2 encoded only the P0 region of the promoter upstream from EGFP. To test the efficacy of insulinotropic protein secretion from recombinant bacteria for stimulating insulin secretion in Caco-2 cells, plasmids pFD-PDX, pFD-GLP, and pFD-20 were constructed as described in Section 6.2.

FIG. 6. P0 and P0/P1 response to glucose. EGFP expression was used to measure the response of the P0 and/or P1 promoter to different media conditions. P0=P0 only; P0+P1=P0 plus P1 flanking region; DH5a=lac operon control. See Section 6.2 for details.

FIG. 7. Secretion of recombinant insulinotropic proteins from *E. coli* Nissle 1917. See Section 6.2 for details.

FIG. 8. Stimulation of insulin secretion in epithelial cells. See Section 6.2 for details.

5. DETAILED DESCRIPTION OF THE INVENTION

Genetically engineered cells and microorganisms are provided for preventing or ameliorating (e.g., treating) diseases through genetically engineered signaling. Therapeutic methods for using the cells and microorganisms to prevent or ameliorate diseases are also provided. The genetically engineered cells (or microorganisms) can be engineered to express a signal of significance to invading microorganisms, to other commensal microorganisms or to the host. In all cases, the engineered commensal microorganism is engineered to emit and/or detect signals on behalf of the host.

In one embodiment, the genetically engineered microorganism can be used to provide quorum-dependent expression of a desirable gene in order to interrupt, prevent, and/or ameliorate a disease of mammals, including, but not limited to a disease of humans. In a particular embodiment, suitable diseases that can be interrupted, prevented and/or ameliorated using the recombinant cells or microorganisms of the invention can include, but are not limited to, parasitic diseases, infectious diseases, autoimmune diseases, and genetic disorders.

As used herein, the term "infectious disease" contemplates diseases that are caused by pathogens of mammals, including without limitation, pathogens such as bacteria, viruses, fungi, and protozoa. A particular example of a bacterial disease of humans that can be interrupted, prevented and/or ameliorated by the engineered cells or microorganisms of the invention includes, but is not limited to, cholera (caused by the marine bacterium *Vibrio cholerae*). More particularly, the recombinant cell or microorganism of the invention can be engineered so that it affects or regulates quorum-dependent expression of virulence factors of. *Vibrio cholerae*. Suitable examples of *Vibrio cholerae* virulence factors that can be inhibited or interfered with by the recombinant cells or microorganisms of the present invention can include, but are not limited to, cholera toxin (CT) and the toxin-coregulated pilus (TCP). Suitable examples of genes that can be inserted into a recombinant cell or microorganism of the present invention (e.g., the commensal bacterium *Escherichia coli* Nissle 1917) to inhibit or interfere with expression of CT or TCP can include, but are not limited to, the *Vibrio cholerae* autoinducers known as cholera autoinducer 1 (CAI-1) (encoded by the cqsA gene) and/or autoinducer 2 (AI-2) (encoded by the luxS gene).

A particular example of an autoimmune disease of humans that can be interrupted, prevented, and/or ameliorated by the engineered cell or microorganism of the invention includes, but is not limited to, Type 1 diabetes. More particularly, with respect to Type 1 diabetes, recombinant cell or microorganism of the invention (e.g., the commensal bacterium *Escherichia coli* Nissle 1917) can be engineered to stimulate the production of insulin and/or insulin transcripts in the human subject.

Examples of gene products that can stimulate insulin production include, but are not limited to, mammalian PDX-1, GIP and Glp-1. PDX-1 has been shown to stimulate constitutive insulin production in epithelia. Glp-1 has been shown to stimulate glucose-responsive insulin production in epithelia. GIP has been shown to stimulate constitutive insulin production in pancreatic beta cells. Therefore, in one embodiment, a commensal bacterium such as *Escherichia coli* Nissle 1917 can be engineered to synthesize peptides of PDX-1, GIP and/or any one of these three peptides or any one of these three peptides in combination with one or all the other peptides.

The present invention contemplates the development and use of microorganisms, e.g., commensal bacterial cell lines that, in one embodiment, can sense conditions in the host organism (e.g., a mammal, a human) and respond with an appropriate or desired therapeutic response or emit a specific signaling molecule on behalf of the host. In other embodiments, the microorganisms may not sense conditions in the host, but may respond with a desired therapeutic response constitutively. Particular examples of engineered commensal bacterial cell lines and their uses are described below for illustrative purposes, but are not meant to limit the scope of the present invention.

For clarity of disclosure, and not by way of limitation, the detailed description of the invention is divided into the subsections set forth below.

5.1 Recombinant Cells

The invention provides an isolated recombinant cell comprising a recombinant nucleic acid encoding a signal, wherein:

the cell is derived from a first organism that is a microorganism, the signal is capable of being expressed by the cell, and the signal regulates signal-dependent expression of a target nucleic acid.

In one embodiment, the nucleic acid is a recombinant quorum nucleic acid.

In another embodiment, the recombinant cell further comprises a recombinant nucleic acid encoding a recombinant response molecule, wherein the recombinant response molecule detects a molecule present in a host.

In another embodiment, the signal is secreted by the cell and secretion by the cell is controlled by an environmental stimulus. In another embodiment, the signal stimulates or inhibits expression of the target nucleic acid.

The environmental stimulus can be secreted by a pathogen, or the presence of the environmental stimulus can be indicative of the pathogen.

In a specific embodiment in which the recombinant cell is used in the treatment of diabetes, the signal can comprise Glp-1, PDX-1 or GIP and the environmental stimulus can be glucose or a sugar that stimulates insulin release within a healthy human.

In another embodiment, the pathogen is an invading pathogen and the signal inhibits or disrupts the pathogenicity or virulence of the invading pathogen.

In another embodiment, the target nucleic acid controls pathogenesis or virulence of a pathogen. In another embodiment, the target nucleic acid encodes a virulence factor of an invading pathogen.

In another embodiment, the target nucleic acid is expressed by a mammal. In another embodiment, the target nucleic acid encodes a mammalian factor. The mammalian factor can, for example, promote normal functioning of a physiological process in a mammalian subject or is effective in preventing onset, establishment, or spread of a non-infectious disease within the mammalian subject.

In another embodiment, the target nucleic acid encodes a disease-causal factor associated with onset of a mammalian non-infectious disease.

A recombinant microorganism (single-celled or multicellular) that comprises one or more recombinant cells that contain a recombinant quorum nucleic acid is also provided. In a specific embodiment, the recombinant quorum nucleic acid is derived from a second organism that expresses a quorum signal (also known as a quorum-sensing signal). The quorum signal regulates quorum-dependent expression of a target nucleic acid. When associated with a host organism (e.g., a commensal host), the recombinant cell (or microorganism comprising the cell), regulates quorum-dependent expression of a gene of interest in the host organism or in an exogenous (e.g., pathogenic) organism.

The recombinant microorganism (or recombinant cell derived therefrom) can be a bacterium, a virus, an archea, a yeast, a fungus or a mammalian cell.

In another embodiment, the recombinant microorganism is non-pathogenic. e.g., a microorganism that belongs to the natural intestinal flora of humans or animals.

In another embodiment, the non-pathogenic microorganism is an aerobic or anaerobic gram-negative bacterium of the intestinal flora.

In another embodiment, the gram-negative bacterium belongs to the genus *Escherichia, Pseudomonas, Bacteroides, Lactobacillus, Lactococcus, Bacillus*, or *Proteus*.

In another embodiment, the gram-negative bacterium is *Escherichia coli* (Nissle 1917).

In another embodiment, non-pathogenic microorganism is an aerobic or anaerobic gram-positive or gram negative bacterium of the intestinal flora.

In another embodiment, the gram-positive bacterium belongs to the genus *Bifidobacterium, Streptococcus, Staphylococcus*, or *Corynebacterium*.

In specific embodiments, the bacterium is an enteric bacterium (e.g. *Escherichia coli, Lactobacillus*) a commensal bacterium (e.g., a strain of *Escherichia coli*). In another specific embodiment, the bacterium is *Escherichia coli* Nissle 1917.

Bacterial strains can be readily obtained using standard methods known in the art. For example, a commensal bacterium such as *Escherichia coli* Nissle 1917 can be obtained from a commercial preparation of the probiotic Mutaflor™. Bacteria can be cultured using standard methods known in the art.

In another specific embodiment in which the disease to be prevented or ameliorated, is Type 1 diabetes, an isolated recombinant cell containing a recombinant nucleic acid encoding a mammalian insulin secretion-stimulating peptide is provided. The recombinant cell can be derived from a microorganism such as an enteric or commensal bacterium of the gut.

According to this embodiment, the mammalian insulin secretion-stimulating peptide regulates expression of insulin in target mammalian insulin-secreting cells. Expression of the mammalian insulin secretion-stimulating peptide by the recombinant cell stimulates glucose-responsive insulin production in a mammalian subject. The mammalian insulin secretion-stimulating peptide can be, e.g., glucagon-like peptide 1 (GLP-1), gastric inhibitory peptide (GIP) or pancreatic and duodenal homeobox gene 1 (PDX-1).

In one embodiment, the target mammalian insulin-secreting cells are intestinal epithelial cells. A recombinant commensal bacterium of the invention can be engineered to stimulate intestinal epithelia cells to secrete insulin in response to glucose. In one embodiment, the bacterium can be engineered to secrete the insulinotropic GLP-1, GIP and/or PDX-1.

5.2 Pathogens

In one embodiment, a target nucleic acid can be expressed by an infectious or invading pathogen including, but not limited to, an infectious bacterium, a protozoan, a fungus or a virus.

A recombinant commensal bacterium of the invention can be engineered to sense the target molecule, which can be, but is not limited to, a quorum signal, and to respond to the molecule by secreting art anti-pathogenic (e.g., antimicrobial, antifungal, etc.) peptide. The anti-pathogenic peptide could be broad band (e.g., affecting several bacterial species) or highly specific to one species of pathogen.

Many infectious pathogens are known in the art. The infectious bacterium can be, for example *E. coli, Pseudomonas* or *Staphylococcus*. The fungus can be, for example *Cryptococcus neoformans*. The virus can be, for example Avian Influenza Virus (H5N1).

In a specific embodiment, the invading pathogen is *Vibrio cholerae*.

5.3 Target Nucleic Acids

In certain embodiments, the target nucleic acid (also referred to herein as an "exogenous" target nucleic acid) can encode a factor of the infectious pathogen, e.g., a virulence factor. In specific embodiments, the factor of the infectious pathogen is a toxin molecule.

In another embodiment, the target nucleic acid encodes a mammalian factor. The mammalian factor can, for example, promote normal functioning of a physiological process in the mammalian subject or be effective in preventing the onset, establishment, or spread of a non-infectious disease within the mammalian subject. In specific embodiments, the mammalian factor is PDX-1, GLP-1 or GIP.

In another embodiment, a quorum-sensing signal regulates expression of a target nucleic acid. For example, the quorum signal can stimulate or inhibit expression of the target nucleic acid.

A method for regulating expression of a target nucleic acid in a host subject is also provided. The method comprises providing an isolated recombinant cell of the invention (or a microorganism comprising or consisting of the cell of the invention) and administering the cell (or the microorganism comprising or consisting of the cell) to the host subject under conditions effective to allow the signal to be expressed in the host subject, thereby regulating signal-dependent expression of the target nucleic acid in the host subject.

5.4 Signals and Nucleic Acids that Encode Them

In one embodiment of the invention, the signal prevents, detects, ameliorates or treats a disease or disorder in a human or animal or cell derived therefrom.

The signal can be secreted, emitted, released or produced by the recombinant cell or microorganism of the invention. Such secretion, emission, release or production by the cell can be controlled by an environmental stimulus.

In one embodiment of the invention, the signal can control, e.g., stimulate or inhibit, expression of the target nucleic acid.

In another embodiment, the signal comprises an antimicrobial peptide or molecule. In another embodiment, the signal comprises an antimicrobial peptide or molecule.

In another embodiment, the signal comprises an antimicrobial peptide or molecule.

In another embodiment, the signal is expressed constitutively by the cell.

In another embodiment, the expression of the recombinant nucleic acid encoding the signal is under the control of an inducible promoter.

In another embodiment, the signal comprises a mammalian insulin secretion-stimulating peptide, the signal regulates expression of insulin in mammalian insulin-secreting cells, and expression of the signal by the cell stimulates glucose-responsive insulin production in a host mammalian subject, e.g., a human. According to this embodiment, the recombinant cell can also comprise an recombinant nucleic acid encoding a recombinant response molecule, wherein the recombinant response molecule detects a molecule present in the host mammalian subject. The mammalian insulin secretion-stimulating peptide can be, e.g., glucagon-like peptide 1 (GLP-1) or pancreatic and duodenal homeobox gene 1 (PDX-1). The mammalian insulin-secreting cells can be intestinal epithelial cells.

In another embodiment, the signal comprises a quorum signal. Quorum signals (also known as quorum sensing signals) are used by microorganisms for density-dependent cell to cell signaling (quorum sensing) to coordinate their growth and virulence. Such signals are well known in the art. For example, both pathogenic and non-pathogenic bacteria in the gut are known to use quorum sensing (Kaper J B, Sperandio V. 2005. Bacterial cell-to-cell signaling in the gastrointestinal tract. Infect Immun 73(6):3197-209).

In a specific embodiment in which the infectious pathogen is *Vibrio cholerae*, the quorum-sensing signal is *Vibrio cholerae* cholera autoinducer 1 (CAI-1) or autoinducer 2 (AI-2). The quorum nucleic acid can comprise a *Vibrio cholerae* cqsA and/or the luxS genes encoding CAI-1 and AI-2, respectively. According to this embodiment, the target nucleic acids encode for *Vibrio cholerae* cholera toxin (CT) and the toxin co-regulated pilus (TCP) and expression of CAI-1 and AI-2 by the recombinant cells will inhibit expression of CT and TCP by *Vibrio cholerae*.

A recombinant cell or microorganism of the invention can be engineered to express a quorum-sensing signal under the control of a promoter (e.g., an inducible or constitutive promoter) using methods well known in the art. The cell or microorganism can be transformed, for example, with a plasmid harboring a quorum gene, to allow for high level expression of the quorum signal.

Genes that encode quorum signals can be obtained using standard nucleic acid amplification methods known in the art, such as high fidelity PCR with primers suitable for the desired amplification. The amplified sequence can be inserted into a suitable vector using standard methods. Such vectors are well known in the art and commercially available (e.g., pUC19 vector (New England Biolabs)). The vector can be transformed into the cell or microorganism by any method known in the art, e.g., electroporation. Cloning can be carried out using standard techniques known in the art (e.g., Sambrook J, Russell D W. 2001. Molecular cloning: a laboratory manual. Cold Spring Harbor, N.Y.: Cold Spring Harbor Laboratory Press. 3 v. p).

In a specific embodiment, a commensal bacterium, *E. coli* Nissle 1917 (Nissle), can be engineered to express CAI-1 under control of the fliC or other constitutive promoter.

5.5 Demonstration of Therapeutic Utility

The recombinant cells or microorganisms of the invention are preferably tested in vitro, and then in vivo, for the desired therapeutic or prophylactic activity, prior to use in humans.

For example, in vitro assays can be used to determine whether administration of a specific recombinant cell or microorganism is indicated. Such assays can be, for example, an in vitro cell culture assay in which a patient tissue sample is grown in culture, and exposed to or otherwise administered a recombinant cell or microorganism, and the effect of such recombinant cell or microorganism upon the tissue sample is observed. A higher level of a desirable effect or a lower level of an undesirable effect indicates that the recombinant cell or microorganism is effective in treating the condition in the patient.

Alternatively, instead of culturing cells from a patient, recombinant cell or microorganism may be screened using cells of a tumor or malignant cell line. Many assays standard in the art can be used to assess levels of desirable or undesirable effects.

In another embodiment of the invention, a recombinant cell or microorganism of the invention is screened for activity to modulate (e.g., promote, inhibit or antagonize) target nucleic acid levels and/or activity. The levels of protein and mRNA encoded by the target nucleic acid and target nucleic acid activity can be determined by any method well known in the art.

For example, protein levels can be quantified by known immunodiagnostic methods such as western blotting immunoprecipitation using any antibody against the protein (for example, commercially available antibodies). mRNA can be quantified by methods that are well known and routine in the art, for example by northern analysis, RNase protection, the polymerase chain reaction in connection with the reverse transcription, etc. Target nucleic acid activity can also be assayed by any method known in the art.

Compounds for use in therapy can be tested in suitable animal model systems prior to testing in humans, including but not limited to in rats, mice, chicken, cows, monkeys, rabbits, etc.

To test the effects of expressing a quorum-sensing signal on the virulence of a pathogen of interest, co-cultures of human epithelia, engineered commensal bacteria and pathogenic bacteria can be made. In these co-cultures, engineered commensal bacteria or either co-cultured first with human epithelia or engineered commensal bacteria are first cultured and then their secretions (cell free media, CFM) are co-cultured with human epithelia. After the engineered commensal bacteria have been in some way co-cultured with epithelia (either by adding them to the epithelia or adding their CFM to the epithelia), a pathogen can be introduced to the epithelia to assess the epithelial reaction to the pathogen.

Assays can be performed to determine the activity of the quorum-sensing signal in the recombinant cell or organism either by immunostaining methods (e.g. ELISA), bioassays (e.g., luminescence), or other wet chemical methods (e.g., high performance liquid chromatography (HPLC)). In one example, bioassays can be used to test for CAI-1 and AI-2 of *Vibrio cholerae*. In this test a strain of *Vibrio* that is mutant for the compound to be tested is engineered to be luminescent in the presence of that compound (either AI-2 or CAI-1). The level of luminescence of the test strain indicates the quantity of the target compound made by the *Vibrio cholerae* being tested.

5.6 Methods for Regulating Signal-Dependent Expression of Target Nucleic Acids A method for regulating signal-dependent expression of a target nucleic acid in an organism is provided. In one embodiment, the method comprise providing the recombinant cell of the invention and administering the cell to the organism under conditions effective to allow the signal to be expressed in the organism, thereby regulating signal-dependent expression of the target nucleic acid in the organism.

In one embodiment, the organism is a mammal. In another embodiment, the mammal is a human.

In another embodiment, the microorganism is a bacterium, such as an enteric bacterium or a commensal bacterium.

In a specific embodiment, the nucleic acid encodes a PDX-1 peptide that is effective in stimulating constitutive insulin production in a mammalian subject. In another embodiment, the nucleic acid encodes a Glp-1 peptide that is effective in stimulating glucose-responsive insulin production in a mammalian subject.

5.7 Methods for Preventing or Ameliorating Diseases or Disorders

The invention provides methods of prevention, amelioration, treatment and/or prophylaxis by administration to a subject of an effective amount of the recombinant cell or microorganism of the invention.

In one embodiment, a method for preventing or ameliorating an infectious or non-infectious disease in a mammalian subject is provided. The method comprises providing an isolated recombinant cell of the invention (or a microorganism comprising or consisting of the cell of the invention); and administering the cell (or a microorganism comprising or consisting of the cell) to the mammalian subject under conditions effective to stimulates expression of the disease-preventing factor or inhibits expression of the causal factor of the disease, thereby preventing or ameliorating the disease.

In one embodiment, the non-infectious disease is an autoimmune disease, e.g., Type 1 diabetes.

In a specific embodiment, the signal comprises PDX-1, the disease-preventing factor is insulin, and PDX-1 stimulates constitutive production of insulin in the mammalian subject. In another specific embodiment, the signal comprises Glp-1, the disease-preventing factor is insulin, and Glp-1 stimulates glucose-responsive insulin in the mammalian subject. In another specific embodiment, the signal comprises GIP, the disease-preventing factor is insulin, and GIP stimulates glucose-responsive insulin in the mammalian subject.

In another embodiment, a method for ameliorating or preventing an infectious disease in a mammalian subject is provided. The method can comprise providing a recombinant cell or microorganism comprising a recombinant cell of the invention (or a recombinant single-celled microorganism comprising the cell), wherein the signal inhibits expression of a virulence factor of an infectious pathogen. The recombinant cell (or a recombinant microorganism comprising the cell or a recombinant single-celled microorganism) can be administered to a mammalian subject under conditions effective to inhibit expression of the virulence factor in the mammalian subject.

In another embodiment, the infectious disease is associated with a virulence factor of an infectious pathogen. Thus, administration of the recombinant cell or microorganism can prevent or ameliorate the infectious disease associated with the virulence factor of the infectious pathogen.

In a specific embodiment, the infectious pathogen is *Vibrio cholerae* and the infectious disease is cholera. The signals can be *Vibrio cholerae* cholera autoinducer 1 (CAI-1) and/or autoinducer 2 (AI-2). The nucleic acid can comprises a *Vibrio cholerae* cqsA gene encoding CAI-1 and/or the luxS gene encoding AI-2. The target nucleic acids can be the *Vibrio cholerae* cholera toxin (CT) and/or the toxin co-regulated pilus (TCP), and expression of CAI-1 and/or AI-2 inhibits expression of CT and/or TCP by the infectious pathogen.

A method of preventing or ameliorating an infectious or non-infectious disease in a mammalian subject is also provided. The method comprises providing a genetically engineered microorganism containing a recombinant nucleic acid that encodes a signaling protein or peptide, wherein the signaling protein or peptide stimulates expression of a disease-preventing factor or inhibits expression of a causal factor of the disease; and administering the microorganism to a mammalian subject under conditions effective to prevent or ameliorate the disease in the mammalian subject. The expression of the signaling protein can be triggered by a signal that exists within the environment that the engineered microorganism is deployed.

The non-infectious disease, can be, for example an autoimmune disease such as Type 1 diabetes or any other non-infectious disease whose presence or possible presence is reflected in the biochemistry of the environment in which engineered commensal bacteria can be deployed.

In a specific embodiment, the signal peptide comprises PDX-1, the disease-preventing factor is insulin, and PDX-1 stimulates constitutive production of insulin in the mammalian subject. Here the triggering signal is glucose, which stimulates the expression and secretion of PDX-1 from the engineered microorganisms. The PDX-1 stimulates the secretion of insulin in the mammalian subject.

In another specific embodiment, the signaling protein is the disease-preventing factor is insulin, and Glp-1 stimulates glucose-responsive insulin in the mammalian subject.

In another specific embodiment, the triggering signal is nitric oxide and indicates the presence of multiple sclerosis in the human host. In this embodiment the engineered microorganism senses higher levels of nitric oxide and responds by fluorescing or luminescing. This provides detection of the higher levels of nitric oxide and serves as an early detection method for multiple sclerosis. The fluorescence or luminescence of the engineered microorganisms can be detected in the stool or in the blood of the human host, depending on the molecule secreted by the engineered microorganism and/or where that organism was introduced to the host (e.g., blood, stomach, etc.).

The invention also provides the use of
an effective material selected from the group consisting of a signal, a fragment thereof, a complex thereof, a derivative thereof, an analog thereof, an expressible nucleic acid coding for the effective material or a fragment or derivative thereof, wherein the signal regulates expression of a target nucleic acid; and
a non-pathogenic microorganism comprising the nucleic acid and capable of expressing the signal.
for the treatment of a disease or disorder of a human or animal subject.

In one embodiment, the signal inhibits or disrupts the pathogenicity or virulence of an invading pathogen. In another embodiment, the signal prevents, detects, ameliorates or treats the disease or disorder in a human or animal subject.

In another embodiment, the disease is an infectious disease or non-infectious disease.

In another embodiment, the treatment takes place by the administration of isolated and purified effective material in a pharmaceutical composition.

In another embodiment, the effective material is administered in a dose which is sufficient to heal the disease state or to prevent it, to stop the progression of the disease or to alleviate symptoms of the disease.

In another embodiment, the effective material is administered orally, rectally, parenterally, by injection, by infusion or by spray or inhaler to the subject.

In another embodiment, the non-pathogenic microorganism is capable of producing the effective material before, during or after administration to the human or animal subject and to release the produced effective material after administration to cells or tissues of the subject.

In another embodiment, the non-pathogenic microorganism is a commensal bacterium or fungus of humans or animals.

In another embodiment, the non-pathogenic microorganism belongs to the natural intestinal flora of humans or animals.

In another embodiment, the non-pathogenic microorganism is an aerobic or anaerobic gram-negative bacterium of the intestinal flora.

In another embodiment, the gram-negative bacterium belongs to the genus *Escherichia, Pseudomonas, Bacteroides, Lactobacillus, Lactococcus, Bacillus*, or *Proteus*.

In another embodiment, the gram-negative bacterium is *Escherichia coli* (Nissle 1917).

In another embodiment, non-pathogenic microorganism is an aerobic or anaerobic gram-positive or gram negative bacterium of the intestinal flora.

In another embodiment, the gram-positive bacterium belongs to the genus *Bifidobacterium, Streptococcus, Staphylococcus*, or *Corynebacterium*.

In another embodiment, the nucleic acid coding for the signal or a fragment or derivative thereof is inserted into a vector.

In another embodiment, the vector is a plasmid, cosmid, bacteriophage or virus.

In another embodiment, the nucleic acid inserted into the vector is under the functional control of at least one regulating element that ensures the transcription of the nucleic acid in a translatable RNA or the translation of the RNA into a protein, before, during or after the administration. In another embodiment, the at least one regulating element is a promoter, a ribosome binding site, a signal sequence or a 3'-transcription terminator.

In another embodiment, the promoter is an inducible promoter. In a specific embodiment, the inducible promoter is induced by a signaling cascade comprising at least one element in response to an environmental stimulus or stimuli.

In another embodiment, the signal sequence is a bacterial or fungal signal sequence that effects the secretion of the protein out of the cytoplasm of the microorganism into the periplasmic space or into the environment of the microorganism.

In another embodiment, the non-pathogenic microorganism is contained in a pharmaceutical or food composition.

In another embodiment, the effective material is administered orally, rectally, parenterally, by injection, by infusion or by spray or inhaler to the subject.

5.8 Therapeutic/Prophylactic Administration and Compositions

The invention provides methods of amelioration, prevention, treatment and/or prophylaxis by administration to a subject of an effective amount of a recombinant cell or microorganism of the invention. In a preferred aspect, the recombinant cell or microorganism of the invention is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Various delivery systems are known and can be used to administer the recombinant cells or microorganisms of the invention, (e.g., liquid suspensions, suspended in food, freeze-dried powders, tablets, capsules, encapsulation in liposomes, microparticles, microcapsules). Methods of introduction include intradermal, intramuscular, intraperitoneal, intravenous, subcutaneous, intranasal, epidural, and oral routes. The recombinant cells or microorganisms may be administered by any convenient route, for example by ingestion, and may be administered together with other biologically active agents. Administration can be systemic or local.

The present invention also provides pharmaceutical compositions. Such compositions comprise a therapeutically effective amount of a recombinant cell or microorganism of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the recombinant cell or microorganism is administered. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will contain a therapeutically effective amount of the recombinant cell or microorganism, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for oral administration to human beings.

The amount of the recombinant cell or microorganism of the invention which will be effective in the treatment of a particular disorder or condition will depend on the nature of the disorder or condition, and can be determined by standard clinical techniques. In addition, in vitro assays may optionally be employed to help identify optimal dosage ranges. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention.

In a specific embodiment, a pharmaceutical or food composition is provided. The composition can comprise at least one cell of a non-pathogenic microorganism capable of producing the effective material and containing an expressible nucleic acid encoding a signal or a fragment or derivative thereof. In one embodiment, the microorganism is an anaerobic or aerobic, gram-negative or gram-positive, bacterium of the intestinal flora. In another embodiment, the microorganism is a commensal bacterium of humans or animals.

In another embodiment, the nucleic acid coding for the signal or a fragment or derivative thereof is inserted into an expression vector, and wherein the expression of the nucleic acid is under the control of at least one regulating element, so that the effective material is expressed before, during or after the administration of the pharmaceutical or food composition, and is released to cells or tissues of a human or animal host after the administration of the pharmaceutical or food composition.

A method for producing a pharmaceutical or food composition is also provided. The method comprises:

(a) isolating or synthesizing a nucleic acid coding for an effective material, wherein the effective material is selected from the group consisting of a signal, a fragment thereof, a complex thereof, a derivative thereof, an analog thereof, an expressible nucleic acid coding for the effective material or a fragment or derivative thereof;

(b) cloning the nucleic acid coding for the signal in a microbial expression vector;

(c) transforming the recombinant expression vector obtained in (b) in a microbial host cell, where the microbial host cell is a commensal of a human or animal host;

(d) propagating the transformed microbial host cells;

(e) producing an immobilized, lyophilized, liquid preparation or suspension of transformed microbial host cells; and (f) mixing the immobilized, lyophilized, liquid preparation or suspension of transformed microbial host cells obtained in (e) with physiologically acceptable excipients, stabilizers, thickeners, parting agents, lubricants, emulsifiers or the like materials to obtain a pharmaceutical or food composition.

The following examples are offered by way of illustration and not by way of limitation.

6. EXAMPLES

6.1 Example 1

Interrupting *Vibrio Cholerae* Infection of Human Epithelial Cells with Engineered Commensal Bacterial Signaling

6.1.1 Introduction

*V. cholerae* El Tor serotypes are largely responsible for outbreaks of cholera in the developing world. The infection cycle for some strains of *V. cholerae* is coordinated, at least in part, through quorum sensing. That is, the expression of virulence genes depends on the concentration of *V. cholerae* autoinducers cholera autoinducer 1 (CAI-1) and autoinducer 2 (AI-2). High concentrations of CAI-1 and AI-2 have been shown previously to inhibit virulence gene expression. This example demonstrates that a commensal bacterium, *E. coli* Nissle 1917 (Nissle), can be engineered to express CAI-1 (Nissle expresses AI-2 natively) and effectively interrupt *V. cholerae* virulence. Nissle was engineered to express CAI-1 under control of the lac promoter, and demonstrated inhibition of *V. cholerae* expression of cholera toxin (CT, as indicated by presence of the CT subunit B (CTB)) and of the toxin co-regulated pilus (TCP, as indicated by the relative transcript of TCP subunit A (TCPA)) in both monocultures of *V. cholerae* and co-cultures with epithelial cells, Nissle, and *V. cholerae*. In the model system of Caco-2 epithelia incubated with *V. cholerae*, we demonstrated that co-cultures with Nissle expressing CAI-1 activity reduced CTB binding to Caco-2 cells by 63% over co-cultures with wild-type Nissle. Further, cultures with Nissle expressing CAI-1 had significantly lower TCPA transcription than controls with wild-type Nissle. These results represent a significant step towards a prophylactic method for combating enteric disease through engineered quorum signaling within a commensal bacterial strain.

6.1.2 Materials and Methods

6.1.2.1 Plasmids

It has been demonstrated that CAI-1 from *V. harveyi* stimulates the *V. cholerae* quorum circuit in an identical fashion as the CAI-1 from *V. cholerae* (Henke J M, Bassler B L. 2004. Three parallel quorum-sensing systems regulate gene expression in *Vibrio harveyi*. J Bacteriol 186(20):6902-14). Hence, the cqsA gene (which encodes for CAI-1) from *V. cholera* (VCA 0532) (Miller M B, Skorupski K, Lenz D H, Taylor R K, Bassler B L. 2002. Parallel quorum sensing systems converge to regulate virulence in *Vibrio cholerae*. Cell 110(3): 303-14) was obtained using high fidelity PCR (Stratagene) with primers: 5' CTG CAG (Pst I site) ATG AAC AAG CCT CAA CTT C 3' and 5' GGT ACC (KpnI site) TTA TTA ACG AAA ATA AAA ATC ACC GTA G 3' and inserted into the pUC19 vector (New England Biolabs). The new vector (pCAI-1) was transformed into *E. coli* Nissle 1917 (Nissle-cqsA) by electroporation. As a control *E. coli* Nissle 1917 were also transformed with pUC19 alone (making Nissle-vector). All cloning was carried out using standard techniques as described previously (Sambrook J, Russell D W. 2001. Molecular cloning: a laboratory manual. Cold Spring Harbor, N.Y.: Cold Spring Harbor Laboratory Press. 3 v. p).

6.1.2.2 Bacterial Strains

*E. coli* Nissle 1917 was obtained from a commercial preparation of the probiotic Mutaflor™. The Nissle 1917 strain was grown on Macconkey agar and confirmed with a series of PCR assays (the primers used were pMut 5/6, 7/8, 9/10 from Blum-Oehler G, Oswald S, Eiteljorge K, Sonnenborn U, Schulze J, Kruis W, Hacker J. 2003. Development of strain-specific PCR reactions for the detection of the probiotic *Escherichia coli* strain Nissle 1917 in fecal samples. Res Microbiol 154(0:59-66).

Nissle 1917 and all other *E. coli* strains were maintained in LB at 37° C., with shaking at 225 rpm. For all virulence expression and infection experiments, a streptomycin-resistant strain of *V. cholerae* El Tor C6706 (kind gift from Ronald Taylor, Dartmouth Medical School) was used. *V. cholerae* were maintained at 30° C. without shaking in either LB or AKFD (15 g/L peptone, 4 g/L yeast extract, 10 g/L sodium chloride. pH 7.4) media. *V. harveyi* strains BB120 (wild type) and BB170 (ΔluxS) were used as positive control and reporter strain for AI-2 assays, respectively. Both strains were maintained in AB medium (0.3M NaCl, 0.05M $MgSO_4$, 0.2% vitamin-free casamino acids (Difco), adjusted to pH 7.5 with KOH. The medium was sterilized and then 10 ml 1M potassium phosphate (pH 7.0), 10 ml of 0.1M L-arginine, 20 ml of Glycerol, 1 ml of 10 µg ml$^{-1}$ riboflavin, and 1 ml of 1 mg ml$^{-1}$ thiamine was added per liter (Greenberg E P, Hastings J W, Ulitzur S. 1979. Induction of Luciferase Synthesis in Beneckea-Harveyi by Other Marine-Bacteria. Archives of Microbiology 120(2):87-91) at 30° C. with shaking at 225 rpm. *V. cholerae* MM920 (*V. cholerae* El Tor C6706 str ΔcqsA ΔluxQ pBB1 (luxCDABE from *V. harveyi*)) was used as the reporter strain for CAI-1 and maintained in LB medium at 30° C. with shaking at 225 rpm.

6.1.2.3 Epithelia

Caco-2 epithelial cells (ATCC #CRL-2102) were maintained in Dulbecco's Modified Eagle Media (DMEM, Cellgro) plus 10% FBS (Cellgro) at 37° C. in a humidified incubator supplemented with 5% $CO_2$. Caco-2 cells were also grown in AKFD supplemented with 10% FBS at 37° C. in a humidified incubator supplemented with 5% $CO_2$ for up to 7 days to determine viability in this medium. All co-culture experiments were performed in AKFD plus 10% FBS with Caco-2 cells in passages between 15 and 22.

6.1.2.4 Co-Culture Conditions

Confluent cultures of Caco-2 cells (passage 15-22) in collagen-treated 96-well plates were washed in fresh AKFD plus 10% FBS and left to incubate overnight at 37° C. in a humidified incubator supplemented with 5% $CO_2$. In order to determine the effects of expressing CAI-1 from Nissle on *V. cholerae*'s virulence, co-cultures of Caco-2 cells and *V. cholerae* with either cell-free medium (CFM) from Nissle strains or Nissle strains themselves were performed as follows.

CFM from Nissle-vector and Nissle-cqsA were obtained as described below ("CFM preparation"). Confluent monolayers of Caco-2 cells in 96-well plates were washed with AKFD once and covered with 200 µL 30% CFM in AKFD with 10% FBS. *V. cholerae* cultures ($OD_{600}$=1) were diluted 1:1,000 into the Caco-2 and CFM-containing wells of 96-well plates, which were incubated at 37° C., 5% $CO_2$ for 3 h. The fluid was removed from the 96-well plates, measured for $OD_{600}$ and centrifuged (12,000×g, 10 min). The supernatant was supplemented with Leupeptin (10 ng/ml), and kept briefly at 4° C. prior to analysis for the B subunit of cholera toxin (CTB). Measurements were normalized by the $OD_{600}$ of the fluid as it was removed from the wells.

For co-cultures with Nissle strains, *V. cholerae* and Caco-2 cells, Caco-2 cells in 96-well plates were washed with AKFD once before adding 200 µL of AKFD plus 10% FBS to each well. Nissle, Nissle-vector and Nissle-cqsA were diluted 1:1, 000 (Starting from $OD_{600}$=1) before being co-incubated with Caco-2 cells for 3 h. 1 mM IPTG was added to Nissle-vector and Nissle-cqsA co-culture medium. After 3 h, a 1:1,000 dilution (Starting from $OD_{600}$=1) of *V. cholerae* was added to each well before incubation for another 3 h. Subsequently, the fluid was removed from the 96-well plates and centrifuged (12,000×g, 10 min). The supernatant post centrifugation was normalized by $OD_{600}$ and supplemented with Leupeptin (10 ng/ml) (added to inhibit proteases), and kept briefly at 4° C. prior to analysis for CTB as described in the "Liposomal CTB Measurements" section. On-cell CTB was analyzed as described in the "On Cell Measurements" section.

6.1.2.5 CFM Preparation

DH5α, Nissle, Nissle-vector, Nissle-cqsA were grown in AKFD with 50 ng/ml ampicillin at 37° C. shaking at 225 rpm for 8 h. *V. cholerae* was grown in AKFD with 10 µg/ml streptomycin at 30° C. at 225 rpm and *V. harveyi* BB120 (ATCC Accession No. BAA-1116) was grown in AB medium, at 225 rpm and 30° C., both for 8 h. After 8 h all bacteria were spun down and washed three times with the corresponding culture medium. All cultures were adjusted to the same $OD_{600}$ and inoculated into the same amount of culture medium. After inoculation DH5α, Nissle, Nissle-vector, Nissle-cqsA were grown overnight in AKFD at 37° C. shaking at 200 rpm. 1 mM IPTG was added to Nissle-vector and Nissle-cqsA culture medium. After inoculation, *V. cholerae* was grown overnight at 30° C. shaking at 200 rpm in AKFD and *V. harveyi* BB120 was grown at 30° C. shaking at 200 rpm in AB medium.

After growing 14 to 16 h, overnights were centrifuged at 4,000×g for 30 min at 4° C. The supernatant was filtered (0.2 µm, PALL life sciences). The cell-free culture medium (CFM) was diluted to $OD_{600}=1$ with AKFD, and 10 ng/ml Leupeptin was added to inhibit proteases before storage at 4° C.

6.1.2.6 AI-2 Activity Assay

*V. harveyi* BB170 (ATCC Accession No. BAA-1117) was grown overnight in AB medium and diluted 1:3,000 in AB medium. Overnights of strains to be tested for AI-2 activity were centrifuged (4,000×g) and 10 µL of their cell-free supernatant was added to 90 µL of diluted *V. harveyi* BB170 in a sterile 96-well plate and incubated at 30° C. with shaking at 225 rpm. Luminescence from the reporter strain was measured in a microtiter plate reader (FLX800, BIO-TEK instruments, Inc., Winooski, Vt.) every 0.5 h until the luminescence of the control increased. As controls we tested the strains *E. coli* DH5α (an AI-2 mutant strain (Surette M G, Miller M B, Bassler B L. 1999. Quorum sensing in *Escherichia coli, Salmonella typhimurium*, and *Vibrio harveyi*: a new family of genes responsible for autoinducer production. Proc Natl Acad Sci USA 96(4):1639-44) that has no CAI-1 activity) and *V. harveyi* BB120 (which has both CAI-1 and AI-2 activity).

6.1.2.7 CAI-1 Activity Assay

*V. cholerae* MM920 was grown to a high density overnight and diluted 1:10 in LB with 5 µg/ml tetracycline. Overnights of strains to be tested for CAI-1 activity were centrifuged (4,000×g) and 30 µL of cell free supernatant was added to 70 µL of diluted *V. cholerae* reporter MM920 (Diluted in LB) in a sterile 96-well plate and incubated at 30° C. with shaking at 225 rpm. Luminescence was measured by microtiter plate reader (FLX800, BIO-TEK Instruments, Inc., Winooski, Vt.) every 0.5 h until the luminescence decreased. As controls we tested the strains *E. coli* DH5α (an AI-2 mutant strain that has no CAI-1 activity) and *V. harveyi* BB120 (which has both CAI-1 and AI-2 activity).

6.1.2.8 RT-PCR for TCPA Expression

CFM from Nissle, Nissle-vector. Nissle-cqsA, and *V. cholerae* was prepared as described above ("CFM preparation"). *V. Cholerae* C6706 str2 (streptomycin resistant) was grown overnight in AKI with streptomycin at 30° C. in the presence of CFM from either Nissle, Nissle-vector, Nissle-cqsA, *V. cholerae* C6707 str2, or LB media only (no CFM). The overnights were diluted 1:10,000 from $OD_{600}=1$ in 5× AKFD medium containing the appropriate CFM plus streptomycin and grown for 3 to 5 h until they reached an $OD_{600}=0.2$ to 0.25. The cultures were then centrifuged (4,000×g) and total RNA was extracted using RNAqueous™ (Ambion, Houston, Tex.) as per manufacturer's instructions, which included DNAse treatment to remove any contaminating DNA. tcpA is the gene that encodes for the A subunit of TCP and the level of tcpA transcript was used as a relative indicator of the amount of TCPA protein expressed. To determine the relative amounts of tcpA mRNA, RT-PCR was performed on each sample with 100 ng total RNA and SuperScript™ III reverse transcriptase (Invitrogen, Carlsbad, Calif.) for first-strand synthesis according to the manufacturer's instructions. Subsequent PCR reactions were performed using a Mastermix™ kit (Promega, Madison, Wis.) and the following primers:

```
                                         [SEQ ID NO: 1]
tcpA forward:    5'-GGT TTG GTC AGC CTT GGT AA-3',

[SEQ ID NO: 2]
reverse:         5'-TGT GAA TGG AGC AGT TCC TG-3';

[SEQ ID NO: 3]
16s RNA forward: 5'-CAG CCA CAC TGG AAC TGA GA-3',

[SEQ ID NO: 4]
reverse:         5'-GTT AGC CGG TGC TTC TTC TG-3'.
```

6.1.2.9 Liposomal CTB Measurement

Liposomes incorporating GM1 ganglioside in the lipid bilayer and encapsulating sulforhodamine B (SRB) (liposomes) were used to detect and quantify cholera toxin subunit B (CTB, as an indicator of CT) in both culture supernatants and on the surface of Caco-2 epithelial cells.

6.1.2.10 CFM Measurements

CFM was prepared as described above ("CFM preparation"). Detection of CTB in CFM was carried out as described previously (Edwards K A, March J C. 2007: GM(1)-functionalized liposomes in a microtiter plate assay for cholera toxin in *Vibrio cholerae* culture samples. Anal Biochem 368(1):39-48). Briefly, CTB was detected using a microtiter sandwich assay. Reacti-bind® Neutravidin linked microliter plates (Pierce Biotechnology, Inc., Rockford, Ill.) were washed with 3×200 µL wash buffer (composed of 0.05% (v/v) Tween-20, 0.01% bovine serum albumin (BSA)). 100 µL biotinylated anti-CTB antibody (10 µg/mL in wash buffer, United States Biological, Swampscott, Mass.) was added and incubated for 2 h at 23° C. Unbound capture antibody was removed, the wells were tapped dry, and washed thoroughly with 3×200 µL wash buffer. Standards composed of purified CTB (EMD Bioscience) in AKFD, LB or supernatants from *V. cholerae* cultures grown in AKFD or LB were diluted 1:1 in a wash buffer and incubated (100 µL per sample per well) in the anti-CTB conjugated plates at room temperature in the dark without shaking for 2 h. The plates were washed twice with 200 µL wash buffer and once with 200 µL 1×Hepes-saline-sucrose (HSS: 10 mM HEPES, 150 mM sodium chloride, 200 mM sucrose, pH 7.5) before applying 100 µL of liposomes diluted in HSS to a concentration of 0.2 mM phospholipid and incubating at room temperature in the dark without shaking for one h. Plates were then shaken for 10 min at 18 Hz in a fluorescence plate reader (FLX800, BIO-TEK Instruments, Inc., Winooski, Vt.). Unbound liposomes were removed from the plates using 3×200 µL HSS. Intact, bound liposomes were lysed with 50 µL 30 mM n-octyl-β-D-glucopyranoside (OG) per well and the fluorescence of each well was measured ($\lambda_{excitation}$=540 nm, $\lambda_{emission}$=590 nm). The data were fit using a 4-parameter logistic (Equation 1):

$$y = b + \frac{a-b}{\left(1 + \left(\frac{x}{c}\right)^d\right)} \quad \text{Equation 1}$$

where x is the CTB concentration (mass volume$^{-1}$), a is the response at zero concentration (RFU), b is the response at maximum concentration (RFU), c is the concentration yielding 50% response (mass volume$^{-1}$) and d is a slope factor (dimensionless) (Gottschalk P G, Dunn J R. 2005. The five-parameter logistic: a characterization and comparison with the four-parameter logistic. Anal Biochem 343(1):54-65).

6.1.2.11 On-Cell Measurements

CTB bound to Caco-2 monolayers was visualized and quantified as described elsewhere (Edwards and March, Anal Biochem. 2008 Sep. 1; 380(1):59-67.). Briefly, standard curves were made by incubating Caco-2 cells with various dilutions of CTB in AKFD plus 10% FBS for 30 min at 37° C. with 5% $CO_2$ without shaking. Cells were then washed with ice cold AKFD plus 10% FBS twice and with ice-cold HSS plus 10% FBS once before adding liposomes and incubating (4° C. without $CO_2$) for 1 h. Excess liposomes were removed from the cells with 3× washes of HSS plus 10% FBS. Washed cells were viewed under a fluorescence microscope (Leica, Basal, Switzerland) and photographed or were lysed with 30 mM OG and read in a fluorescence microtiter plate reader (FLx800, Biotek Instruments). For measuring CTB binding to Caco-2 monolayers in co-cultures, post incubation bacteria were washed from the Caco-2 cells with ice-cold AKFD plus 10% FBS twice and with ice-cold HSS plus 10% FBS once before the amount of CTB binding was estimated with liposomes against a standard curve of pure CTB as described above.

6.1.2.12 Microscopy

Caco-2 monolayers were visualized under 40× magnification using a standard fluorescence light microscope (Leica, Basel, Switzerland). Images were obtained using a monochrome camera (Retiga 4000R, Qimaging, Inc., Surrey, BC, Canada).

6.1.3 Results and Discussion

6.1.3.1 Transformation of *E. Coli* Nissle 1917 with cqsA

Nissle was transformed with a plasmid harboring the *V. cholerae* quorum gene, cqsA (making the strain Nissle-cqsA) to allow for high level expression of the *V. cholerae* quorum signal, CAI-1. To test if Nissle was exhibiting CAI-1 activity and AI-2 activity, a bioassay was performed.

FIG. 2 shows expression of autoinducers in engineered commensal bacteria. *E. coli* Nissle 1917 (Nissle) was transformed with either an empty vector (Nissle-vector) or with a vector carrying cqsA (Nissle-cqsA). Cells were tested for their ability to express (A) AI-2 or (B) CAI-1. *E. coli* DH5α (DH5a), *V. cholerae* (VC) and *V. harveyi* (BB120) were used as controls. DH5α is mutant for AI-2 activity. Error bars represent one standard deviation of triplicate samples. The results indicated that Nissle had as much AI-2 activity as *V. cholerae* (FIG. 2A), and when transformed with pUC19-cqsA exhibited along the same order of magnitude of CAI-1 activity as *V. cholerae* following stimulation with IPTG (FIG. 2B).

6.1.3.2 Interruption of *V. Cholerae* Virulence in Monocultures with CFM

To test the ability of the transformed Nissle to inhibit *V. cholerae* virulence, *V. cholerae* was incubated with CFM from Nissle, Nissle-vector, Nissle-cqsA and LB medium only. Total RNA was extracted from the cultures after 3 to 5 h and assayed for tcpA transcript using RT-PCR and 100 ng of total RNA per sample (FIG. 3A).

FIG. 3 shows interruption of *V. cholerae* virulence in culture media. *E. coli* Nissle 1917 (Nissle) was transformed with either an empty vector (Nissle-vector) or with a vector carrying cqsA (Nissle-cqsA). *V. cholerae* were grown in cell free medium (CFM) from each of these strains or in CFM from *V. cholerae* (VC) or in sterile media (Media only). Following incubation with the various CFMs, *V. cholerae* tcpA transcripts were analyzed using RT-PCR (FIG. 3A). tcpA transcripts were used as an indicator of the relative amount of TCPA protein expressed. Results are normalized by 16 s RNA transcript amounts. CTB expression was monitored after incubation of *V. cholerae* with CFM from the strains indicated (FIG. 3B). As a positive control for both TCPA and CTB experiments, *V. cholerae* was incubated in fresh media without CFM. Error bars represent one standard deviation of triplicate samples. p values are from a student's T-test.

Gels were scanned and analyzed with Image J (National Institutes of Health, Bethesda, Md.) software to determine the relative amounts of transcript between them. 16 s RNA was used to normalize the results. It was observed that CFM from Nissle-cqsA had a similar effect on TCPA expression as did CFM from *V. cholerae*. These results were expected, as it has already been established that TCPA expression is quorum sensing dependent.

To test if Nissle-cqsA CFM could inhibit *V. cholerae* CT expression in culture, we assayed for CT's B subunit (CTB) expression using GM1 ganglioside-functionalized liposomes as described previously (Edwards K A, March J C. 2007. GM(1)-functionalized liposomes in a microtiter plate assay for cholera toxin in *Vibrio cholerae* culture samples. Anal Biochem 368(1):39-48). The results (FIG. 3B) indicated that CT can be greatly decreased in monocultures of *V. cholerae* grown with CFM from Nissle, Nissle-vector, and Nissle-cqsA. This result was surprising, given the TCPA results in which the only reduction similar to *V. cholerae* CFM was seen with Nissle-cqsA CFM. This was observed throughout several replicate experiments (data not shown). Although the CT level was on average lower for Nissle-cqsA, it was not anticipated that the level of CT expression would be lower for CFM incubations with Nissle and Nissle-vector than it was for CFM from *V. cholerae*. This result may have been due to AI-2 activity in the Nissle CFM and residual CT in *V. cholerae* CFM.

6.1.3.3 Interruption of *V. Cholerae* Virulence in Epithelial Co-Cultures

To determine if Nissle-cqsA would be capable of preventing *V. cholerae* infection of epithelia, we developed a simple culture model that consisted of Caco-2 epithelial cells, *V. cholerae*, and either Nissle strains or Nissle CFM. Since *V. cholerae* do not produce CT at appreciable levels in DMEM (Edwards K A, March J C. 2007. GM(1)-functionalized liposomes in a microtiter plate assay for cholera toxin in *Vibrio* cholerae culture samples. Anal Biochem 368(1):39-48), we determined that Caco-2 cells can continue to grow for at least 1 week in AKFD plus 10% FBS (data not shown). Hence, we performed all co-culture experiments in AKFD plus 10% FBS.

Results from culturing Caco-2 cells in CFM from either Nissle-vector or Nissle-cqsA and then co-culturing with *V. cholerae* are summarized in FIG. 4.

FIG. 4 shows interruption of *V. cholerae* virulence in co-cultures. *E. coli* Nissle 1917 (Nissle) was transformed with either an empty vector (Nissle-vector) or with a vector carrying cqsA (Nissle-cqsA). Caco-2 epithelial cells were incubated with either CFM from various Nissle strains (FIG. 4A) or with the Nissle strains themselves (FIGS. 4B-4D) and with *V. cholerae* before assaying for CTB either in the supernatant (FIG. 4A) and (FIG. 4B) or attached to the Caco-2 cells (FIG. 4C) and (FIG. 4D). CTB amounts were estimated from controls of known amounts of CTB applied to Caco-2 cells. Error bars represent one standard deviation of triplicate samples. p values are from a student's T-test. Panel pictures in FIG. 4D are taken with an ordinary fluorescence microscope. Fluorescence indicates CTB bound to Caco-2 cells.

After *V. cholerae* were incubated with the Caco-2 cells for 3 h the amount of CT in the culture medium (FIG. 4A) was quantified. The amount of CT in the culture supernatant was clearly reduced in the presence of Nissle-cqsA over the controls. It was then tested whether co-cultures of Nissle strains with Caco-2 cells would yield similar outcomes. Nissle-vector and Nissle-cqsA strains were co-cultured with Caco-2 cells for 3 h before culturing with *V. cholerae* for 3 h. We measured again both CT in the culture medium (FIG. 4B) and adhered to Caco-2 cells (FIG. 4C). Caco-2 cells were viewed under a fluorescence microscope to visualize CT binding (FIG. 4D). It was concluded from these experiments that the level of CT expression and binding to Caco-2 cells was significantly different between cells treated with Nissle-cqsA and those treated with Nissle-vector carrying the empty vector. The presence of the Nissle-cqsA reduced expression of CT in the *V. cholerae* strain and resulted in less CT binding to the Caco-2 cells.

6.1.4 Conclusions

From these in vitro results, it can be expected that Nissle-cqsA, if taken prophylactically, could limit *V. cholerae* colonization of a human GI tract. Considering the amounts of bacteria used (nearly a 1:1 ratio of commensal bacteria and *V. cholerae*) and the time scale involved (3 h for establishment of commensal bacteria with the epithelial layer), the results indicate that, if the commensal bacteria described in this example are taken as a prophylactic, the number of commensal bacteria established in the GI tract ($\sim 10^{11}$ CFU $g^{-1}$ intestinal contents. (Schultz M, Watzl S, Oelschlaeger T A, Rath H C, Gottl C, Lehn N, Scholmerich J, Linde H J. 2005. Green fluorescent protein for detection of the probiotic microorganism *Escherichia coli* strain Nissle 1917 (EcN) in vivo. J Microbiol Methods 61(3):389-98), will greatly outnumber the amount of *V. cholerae* in a contaminated water sample ($\sim 10^4$-$10^8$ CFU $mL^{-1}$, (Baselski V S, Medina R A, Parker C D. 1978. Survival and multiplication of *Vibrio cholerae* in the upper bowel of infant mice. Infect Immun 22(2):435-40). Hence, it is expected that *V. cholerae* virulence would be diminished to the extent that was seen with pure overnight cultures (FIG. 3). This amount of inhibition is similar to what can be expected when *V. cholerae* reaches a high density within the host and interrupts virulence.

This example demonstrates that a commensal bacterial strain (*E. coli* Nissle 1917) can be engineered to serve as a prophylactic for cholera. Engineered commensal bacteria have tremendous potential for use as drug delivery vehicles, especially in the developing world where barriers to accessing pharmaceuticals are potentially higher than those to obtaining food aid. This example demonstrates that commercially available human commensal bacterial strains can be engineered to mimic invasive pathogen signaling in such a way as to interrupt virulence. This is a key distinction from other work reported in the relatively new area of commensal bacterial engineering. Using the above-described method, commensal strains can be engineered to serve as important signal relays, expressing a pathogen-specific bacterial quorum signal in such a way as to prevent virulence factors from being expressed once inside the host.

Using this approach, commensal strains can be engineered to communicate with other invasive species or even with species already established in the GI tract. Aspects of metabolism may be altered in response to specific changes in GI tract biochemistry.

While the use of recombinant organisms in this regard (i.e. within humans) may be a cause for concern, commensal strains (which are generally regarded as safe by the Food and Drug Administration) can be used safely for expressing exogenous genes. Not only is the likelihood of horizontal gene transfer lower for commensal strains versus adenoviruses since adenoviruses facilitate nuclear encapsulation of the heterologous genes, but in the case of commensal bacteria, antibiotics can be used to eliminate them completely from the GI tract. This technology is therefore considered as safe as, or safer than, some already approved technologies for human use.

6.2 Example 2

Secreting Insulinotropic Proteins from Commensal Bacteria: Rewiring the Gut to Treat Diabetes

6.2.1 Summary

Example 1 (above) demonstrated that *E. coli* Nissle 1917 (an over the counter probiotic strain, Nissle) can be engineered for the expression of a *Vibrio cholerae* quorum sensing signal, creating a potential prophylactic for cholera (Duan, F., and J. C. March. 2008. Interrupting *Vibrio cholerae* infection of human epithelial cells with engineered commensal bacterial signaling. Biotechnol Bioeng. 101(1):128-134, DOI: 10.1002/bit.21897).

The present example demonstrates that commensal bacteria can stimulate intestinal epithelia cells to secrete insulin in response to glucose. Commensal strain *E. coli* Nissle 1917 were engineered to secrete the insulinotropic proteins GLP-1 and PDX-1. Epithelia stimulated by engineered strains and glucose secreted up to 1 ng $mL^{-1}$ of insulin with no significant background secretion.

6.2.2 Introduction

Two proteins, glucagon-like peptide 1 (GLP-1) and pancreatic and duodenal homeobox gene 1 (PDX-1) have been shown recently to stimulate intestinal epithelial cells to synthesize insulin in response to glucose (Suzuki, A., H. Nakauchi, and H. Taniguchi. 2003. Glucagon-like peptide 1 (1-37) converts intestinal epithelial cells into insulin-producing cells. Proc Natl Acad Sci USA 100:5034-9) and irrespective of glucose levels (Yoshida, S., Y. Kajimoto, T. Yasuda, H.

Watada, Y. Fujitani, H. Kosaka, T. Gotow, T. Miyatsuka, Y. Umayahara, Y. Yamasaki, and M. Hori. 2002. PDX-1 induces differentiation of intestinal epithelioid IEC-6 into insulin-producing cells. Diabetes 51:2505-2513), respectively. GLP-1 is secreted by intestinal epithelia of the distal small bowel in response to glucose and other nutrients (Baggio, L. L., and D. J. Drucker. 2007. Biology of incretins: GLP-1 and GIP. Gastroenterology 132:2131-57). It has a very short half life and its degradation by dipeptidylpeptidase IV (DPP-IV) occurs in the blood vessels draining the intestinal mucosa (Hansen, L., C. F. Deacon, C. Orskov, and J. J. Hoist. 1999. Glucagon-like peptide-1-(7-36) amide is transformed to glucagon-like peptide-1-(9-36) amide by dipeptidyl peptidase IV in the capillaries supplying the L cells of the porcine intestine. Endocrinology 140:5356-63). GLP-1 activates insulin synthesis in pancreatic β cells by binding to the membrane receptor, GLP-1R, and has been suggested as a therapeutic for treating both type-1 (Suzuki, A., H. Nakauchi, and H. Taniguchi. 2003. Glucagon-like peptide 1 (1-37) converts intestinal epithelial cells into insulin-producing cells. Proc Natl Acad Sci USA 100:5034-9) and type-2 diabetes (Baggio, L. L., and D. J. Drucker. 2007. Biology of incretins: GLP-1 and GIP. Gastroenterology 132:2131-57).

Suzuki and co-workers demonstrated that intestinal epithelial cells in both neonatal and adult rats injected intra-peritoneal with GLP-1 became glucose-responsive insulin-secreting cells (Suzuki, A., H. Nakauchi, and H. Taniguchi. 2003. Glucagon-like peptide 1 (1-37) converts intestinal epithelial cells into insulin-producing cells. Proc Natl Acad Sci USA 100:5034-9). In addition, they found that surgical implantation into mice of epithelial cells stimulated in vitro with GLP-1 resulted in reversal of diabetes mellitus in mice receiving the implants.

The transcriptional activator PDX-1 has been shown to stimulate insulin secretion in both β cells and intestinal epithelia (Koizumi, M., R. Doi, K. Fujimoto, D. Ito, E. Toyoda, T. Mori, K. Kami, Y. Kawaguchi, G. K. Gittes, and M. Imamura. 2005. Pancreatic epithelial cells can be converted into insulin-producing cells by GLP-1 in conjunction with virus-mediated gene transfer of pdx-1. Surgery 138:125-133; Koizumi, M., K. Nagai, A. Kida, K. Kami, D. Ito, K. Fujimoto, Y. Kawaguchi, and R. Doi. 2006. Forced expression of PDX-1 induces insulin production in intestinal epithelia. Surgery 140:273-280). Koizumi and coworkers have shown that when pancreatic epithelia are virally transfected with pdx-1 and concurrently stimulated with exogenous GLP-1 they become insulin secreting cells (Koizumi, M., R. Doi, K. Fujimoto, D. Ito, E. Toyoda, T. Mori. K. Kami, Y. Kawaguchi, G. K. Gittes, and M. Imamura. 2005. Pancreatic epithelial cells can be converted into insulin-producing cells by GLP-1 in conjunction with virus-mediated gene transfer of pdx-1. Surgery 138: 125-133). The same group demonstrated that intestinal epithelia (mouse ileal loops) express insulin when transfected with pdx-1, although in that paper no data was presented on the addition of GLP-1 to these cells (Koizumi. M., K. Nagai, A. Kida, K. Kami, D. Ito, K. Fujimoto, Y. Kawaguchi, and R. Doi. 2006. Forced expression of PDX-1, induces insulin production in intestinal epithelia. Surgery 140:273-280).

Supplemental gut bacteria are widely available as "probiotics," and are generally regarded as safe (GRAS) by the Food and Drug Administration (Ahmed, F. E. 2003. Genetically modified probiotics in foods. Trends in Biotechnology 21:491-497). Potential advantages of using commensal strains for in vivo recombinant gene expression include their compatibility with the host (particularly the host's immune system), their controllable persistence in the gut and their ability to be orally dosed. Commensal bacterial expression of various recombinant cytokines and antigens in animal models has been reported (Daniel, C., A. Repa, C. Wild, A. Pollak, B. Pot, H. Breiteneder, U. Wiedermann, and A. Mercenier. 2006. Modulation of allergic immune responses by mucosal application of recombinant lactic acid bacteria producing the major birch pollen allergen Bet v 1. Allergy 61:812-819; Farrar, M. D., T. R. Whitehead, J. Lan, P. Dilger, R. Thorpe, K. T. Holland, and S. R. Carding. 2005. Engineering of the gut commensal bacterium Bacteroides ovatus to produce and secrete biologically active murine interleukin-2 in response to xylan. Journal of Applied Microbiology 98:1191-1197; Hartmann, M., A. Westendorf, J. Buer, and F. Gunzer. 2004. *E-coli* Nissle 1917 as a vehicle for intestinal expression of therapeutic molecules: Construction of an *E-coli* a hemolysin based expression vector. International Journal of Medical Microbiology 294:198-198; Hazebrouck, S., L. Pothelune, V. Azevedo, G. Corthier, J.-M. Wal, P. Langella 2007. Efficient production and secretion of bovine β-lactoglobulin by *Lactobacillus casei*. Microb Cell Fact. 2007; 6: 12. doi: 10.1186/1475-2859-6-12).

6.2.3 Materials and Methods

Plasmid Construction

All cloning was performed using techniques described previously (Sambrook, J. & Russell, D. W. Molecular cloning: a laboratory manual, Edn. 3rd., Cold Spring Harbor Laboratory Press, Cold Spring Harbor, N.Y.; 2001). FIG. 5 provides a schematic of plasmids used in this study. To study the P0/P1 promoters from *E. coli* DH5α two plasmids were made (pFD1 and pFD2). pFD1 encoded the entire P0/P1 region to drive the expression of enhanced green fluorescent protein (EGFP). pFD2 encoded only the P0 region of the promoter upstream from EGFP. To test the efficacy of insulinotropic protein secretion from recombinant bacteria for stimulating insulin secretion in Caco-2 cells, plasmids pFD-PDX, pFD-GLP, and pFD-20 were constructed as described herein.

Figure 6:
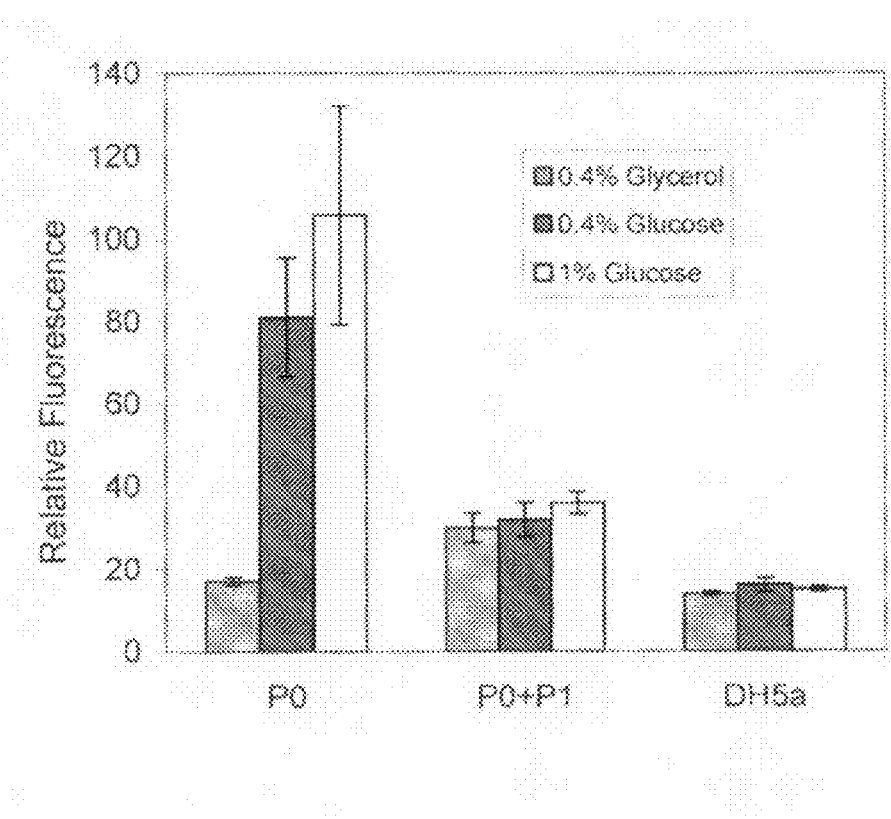

FIG. 6 shows P0 and P0/P1 response to glucose. EGFP expression was used to measure the response of the P0 and/or P1 promoter to different media conditions. P0=P0 only; P0+P1=P0 plus P1 flanking region; DH5a=lac operon control.

To test the efficacy of the glucose-responsive promoter system to produce recombinant proteins in response to glucose, two lengths of the glucose-responsive promoter region from *E. coli* DH5α were TA cloned into pGlow-GFP upstream and in-frame with GFP (results in FIG. 6). The two constructs consisted of the P0 promoter or the region spanning both the P0 and P1 promoters (Ryu, S. & Garges, S. Promoter Switch in the *Escherichia-Coli* Pts Operon. Journal of Biological Chemistry 269, 4767-4772 (1994)) in frame and upstream from the GFP start. Briefly, the P0 region was cloned from the genomic DNA of *E. coli* DH5α into pGLOW-GFP (Invitrogen, Carlsbad, Calif.) to make (pFD2). The P0/P1 region was cloned into pGLOW-GFP to make pFD1.

In order to express the mammalian PDX-1 gene in Nissle, the plasmid pFD-PDX was constructed as follows. The expression cassette 6× His-Xpress-EK-PDX-1-CPP was obtained using two rounds of high fidelity PCR (Stratagene, La Jolla, Calif.). The full length FLIC was obtained from DH5α via high fidelity PCR. These two fragments were cloned into pBluescript-KS to create 6× His-Xpress-EK-PDX-1-CPP-FLIC. The 6× His-Xpress-EK-PDX-1-CPP-FLIC fragment was then cloned into pGLOW-P0-GFP to create a vector (pFD-PDX) that uses the P0 promoter of *E. coli* to drive the expression of 6× His-Xpress-EK-PDX-1-CPP-FLIC.

In order to express the protein GLP-1 constitutively in Nissle the plasmid pFD-GLP was constructed as follows. The sequence 6× His-Xpress-EK-GLP-1 (1-37) was made synthetically (IDT, Coralville, Iowa). This fragment was inserted via high fidelity PCR into pBluescript-KS to make pBluescript-GLP. High fidelity PCR was used to clone the 5'UTR-FLIC20 sequence from pKS104 into pBluescript-GLP to make pBluescipt-20-GLP. The resultant vector contained the sequence: 5'UTR-FLIC20-6× His-Xpress-EK-GLP-1 (1-37). This sequence was cloned into pKS121 (containing the 3'UTR of FLIC) to obtain the construct: 5'UTR-FLIC20-6× His-Xpress-EK-GLP-1 (1-37)-3'UTR by high fidelity PCR.

To obtain pFD-20, high fidelity PCR was used to clone the 5'UTR-FLIC20-6× His-Xpress-EK sequence from pFD-GLP. The PCR fragment was cloned into pKS121 to obtain the construct: 5'UTR-FLIC20-6× His-Xpress-EK. pKS104 and pKS121 were obtained from (University of Helsinki, Finland, Laboratory of Benita Westerlund-Wikström).

Bacterial Strains

*E. coli* Nissle 1917 was obtained from a commercial preparation of the probiotic Mutaflor™ as described previously (Duan, F., and J. C. March. 2008. Interrupting *Vibrio cholerae* infection of human epithelial cells with engineered commensal bacterial signaling. Biotechnol Bioeng. 101(1):128-134, DOI: 10.1002/bit.21897) Nissle 1917 and all other *E. coli* strains were maintained in LB at 37° C. with shaking at 225 rpm. For co-culture experiments, Nissle 1917 was grown in F-12K (Cellgro, Manassas, Va.) supplemented with 0.4% Glycerol or 0.4% Glucose at 37° C., with shaking at 225 rpm or without shaking.

Cell Culture Conditions

Caco-2 epithelial cells (ATCC #CRL-2102, Manassas, Va.) were maintained in Dulbecco's Modified Eagle Media (DMEM, Cellgro, Herndon, Va.) plus 10% FBS (Cellgro) at 37° C. in a humidified incubator supplemented with 5% $CO_2$. Caco-2 cells were also grown in F-12K supplemented with 10% FBS at 37° C. in a humidified incubator supplemented with 5% $CO_2$. All co-culture experiments were performed in F-12K plus 10% FBS with Caco-2 cells in passages between 15 and 22.

CFM-Culture Conditions

CFM from Nissle harboring pFD-20 (Nissle vector), pFD-PDX (Nissle-PDX-1) and pFD-GLP (Nissle-GLP-1) were obtained as described below ("CFM preparation"). For co-culturing, approximately 80% confluent monolayers of Caco-2 cells in 12-well plates were washed with fresh F-12K plus 10% FBS once and covered with 1 mL 50% CFM in F-12K with 10% FBS and incubated at 37° C. with 5% $CO_2$. 200 nM GLP-1 (1-37) (Bachem, King of Prussia, Pa.) was added for positive control wells. Following a 16 h incubation, an additional 1 mL of 50% CFM in F-12K with 10% FBS or 1 mL F-12K with 10% FBS plus 200 nM GLP-1 (1-37) was added to the cells, supplemented with 0.4% Glucose or 0.4% Glycerol before incubation for an additional 2 h. The media was removed from the cells, supplemented with Leupeptin (10 ng/mL), 0.2 mM PMSF and aprotinin (10 ng/mL), centrifuged (12,000×rpm) (Effendorf 5804R, Westbury, N.Y.), and kept briefly at 4° C. prior to ELISA analysis for insulin expression (see "immuno-blot and ELISA" section). RT-PCR analysis for insulin expression was performed on the cells immediately following media removal as follows (See "RT-PCR for insulin expression").

CFM Preparation

Nissle-vector and Nissle-GLP-1 were grown in F-12K plus 0.4% Glycerol and Nissle-PDX-1 was grown in F-12K plus 0.4% Glucose at 37° C. shaking at 225 rpm for 24 h. After 24 h all bacteria were diluted to an $OD_{600}$=1 with F-12K, spun down and discarded. The supernatant was filtered (0.2 μm, PALL Life Sciences, Cornwall, UK). The cell-free culture medium (CFM) was supplemented with 10 ng/ml leupeptin, 200 μM PMSF and 5 ng/mL aprotinin to inhibit proteases prior storage at 4° C.

RT-PCR

Total RNA from Caco2 cells were extracted at the end of each experiment using RNAqueous™ (Ambion. Houston, Tex.) as per manufacturer's instructions, which included DNAse treatment to remove any contaminating DNA. To determine the relative amounts of insulin mRNA, RT-PCR was performed on each sample with 500 ng total RNA and SuperScript™ III reverse transcriptase (Invitrogen, Carlsbad, Calif.) for first-strand synthesis according to the manufacturer's instructions. Subsequent PCR reactions were performed using a Quick Load Taq 2× Master Mix (NEB) and the following primers: Human insulin forward: 5'-AGCACAT-CACTGTCCTTCTGCCAT-3' [SEQ ID NO: 5], reverse: 5'-TTGTTCCACAATGCCACGCTTCTG-3'[SEQ ID NO: 6]; Human β-Actin forward: 5'-ATCTGGCACCACACCT-TCTACAATGAGCTGCG-3'[SEQ ID NO: 7], reverse: 5'-CGTCATACTCCTGCTTGCTGATCCACATCTG-3' [SEQ ID NO: 8].

Precipitation of Secreted Proteins and Preparation of Cell Lysates

Nissle-vector and Nissle-GLP-1 were grown in F-12K plus 0.4% Glycerol and Nissle-PDX-1 was grown in F-12K plus 0.4% Glucose or 0.4% Glycerol at 37° C. shaking at 225 rpm for 24 h. After 24 h all bacteria were centrifuged. The supernatant was filtered (0.2 μm, PALL Life Sciences). The cell-free culture medium (CFM) was diluted to the same OD600 with F-12K, and 10 ng/ml leupeptin, PMSF and 5 ng/mL aprotinin was added to inhibit proteases. Clarified supernant (14 ml) was precipitated with 10% trichloroacetic acid (TCA, VWR) for 30 min on ice, and the pellet was washed twice in ice-cold ethanol/ether (1:1). The supernatant pellet was dried under vacuum, dissolved in 50 μl sample buffer (2% SDS, 50 mM Tris, pH 6.8, 20% glycerol, 10% mercaptoethanol, bromophenol blue) and boiled for 5 min at 95° C. The cell pellet was resuspended (From 14 ml culture) in room temperature BugBuster Master Mix by gentle vortexing, using 500 μl BugBuster Master Mix with protease inhibitors (10 ng/ml Leupeptin, 200 μM PMSF and 5 ng/mL aprotinin). The cell suspension was incubated on a shaking platform (VWR, Bristol, Conn.) at a slow setting for 10-20 min at room temperature. 125 μl 5× sample buffer was added to each sample before and boiling for 10 min at 95° C.

Immuno-Blot and ELISA

To estimate the amounts of GLP-1 and PDX-1 expression and secretion, standard techniques for western blotting were used (Sambrook, J. & Russell, D. W. Molecular cloning: a laboratory manual. Edn. 3rd. Cold Spring Harbor Laboratory Press, Cold Spring Harbor, N.Y.; 2001). Briefly, 50 μl samples were loaded on a polyacrilamide gel and blotted onto Immobilon-P$^{SQ}$ Transfer membrane. Membranes were probed with 1:1,000 for mouse anti-his (GE health, Piscataway, N.J.). The membranes were incubated with HRP-conjugated Anti-mouse IgG (Amersham Biosciences, Pittsburgh, Pa.), developed by enhanced chemiluminescence (Pierce, Rockford, Ill.) and exposed onto X-Ray film (Phoenix, Candler, N.C.). Blot films were scanned and the images analyzed for blot pixel density using Image J software (NCBI).

To estimate the amount of insulin secreted from Caco-2 cells, cell free supernatants (obtained as described in "CFM-culture conditions") were assayed using standard ELISA procedures (Sambrook, J. & Russell, D. W. Molecular cloning: a laboratory manual, Edn. 3rd., Cold Spring Harbor Laboratory Press, Cold Spring Harbor, N.Y.; 2001) with capture (E86802M at 5 μg/mL) and biotinylated detection (E86306B at 1 μg/mL) antibodies both from Biodesign (Saco, Me.) in Num (Rochester, N.Y.) Immobilizer Amino™ plates. For detection, streptavidin-conjugated horseradish peroxidase (1:5,000) was applied to the samples after the biotinylated detection antibody. The detection substrate was Amplex Ultra-Red™ reagent (Invitrogen, Carlsbad, Calif.) used as per manufacturer's instructions. Fluorescence was detected in an FLX-800 plate reader (Biotek, Burlington, Vt.) at λ=540 nm (excitation) and λ=590 nm (emission). Standards of human insulin (Sigma, St. Louis, Mo.) from 0 to 2 ng mL$^{-1}$ were made in quintuplicate for each plate to insure accuracy. Each sample was measured in five separate wells to insure analytical precision.

Calculations for Scaling Insulin Response to Body

To extrapolate the response from the cell culture model to what might be possible in the body it was assumed that only the small intestine would be stimulated to secrete insulin. Work by Rao and coworkers demonstrated that survivability for recombinant Nissle in mouse small intestines was $10^6$ cfu/g tissue after 3 days (Rao, S. et al. 2005. Toward a live microbial microbicide for HIV: Commensal bacteria secreting an HIV fusion inhibitor peptide. Proceedings of the National Academy of Sciences of the United States of America 102, 11993-11998). However, work by Westendorf and co-workers found 3 orders of magnitude higher recombinant Nissle concentrations in the feces of mice than did Rao, indicating that there is likely variation in survivability based on the proteins being secreted (Westendorf, A. M. et al. 2005. Intestinal immunity of *Escherichia coli* NISSLE 1917: a safe carrier for therapeutic molecules. Ferns Immunology and Medical Microbiology 43, 373-384). Westendorf did not give a value for the survivability of Nissle in the small intestine. Assuming a survivability in the human system (from whence Nissle was isolated) of somewhere between $10^6$ and $10^9$ cfu mL$^{-1}$ ($10^9$ cfu mL$^{-1}$ corresponds to an $OD_{600}$=1 in our experiments) our estimates for the amount of insulin that might make it into the blood stream if our bacteria were colonizing the small intestine were as follows. The amount secreted in these experiments (~1 ng/mL×1 mL/well×1 well/491 mm$^2$ gives 0.002 ng/mm$^2$) was multiplied by mucosal surface area of the small intestine (~2 m$^2$ from Wilson, J. P. 1967 Surface Area of Small Intestine in Man. Gut 8, 618) to get a range of insulin in the blood (assumed to be 4.7 L) of 164 fmol L$^{-1}$ to 164 pmol L$^{-1}$ for Nissle survivability ranging from $10^6$ to $10^9$ cfu mL$^{-1}$, respectively. Postprandial serum insulin concentrations can be as high as 400 pmol L$^{-1}$ for adult non-diabetics (Basu, R. et al. 2006. Effects of age and sex on postprandial glucose metabolism: differences in glucose turnover, insulin secretion, insulin action, and hepatic insulin extraction. Diabetes 55, 2001-2014).

6.2.4 Results and Discussion

Nissle was engineered to secrete either GLP-1 (amino acids 1 through 37) or the full length PDX-1 using the fliC secretion tag (Majander, K., L. Anton, J. Antikainen, H. Lang, M. Brummer, T. K. Korhonen, and B. Westerlund-Wikstrom, 2005. Extracellular secretion of polypeptides using a modified *Escherichia coli* flagellar secretion apparatus. Nature Biotechnology 23:475-481).

Figure 7:
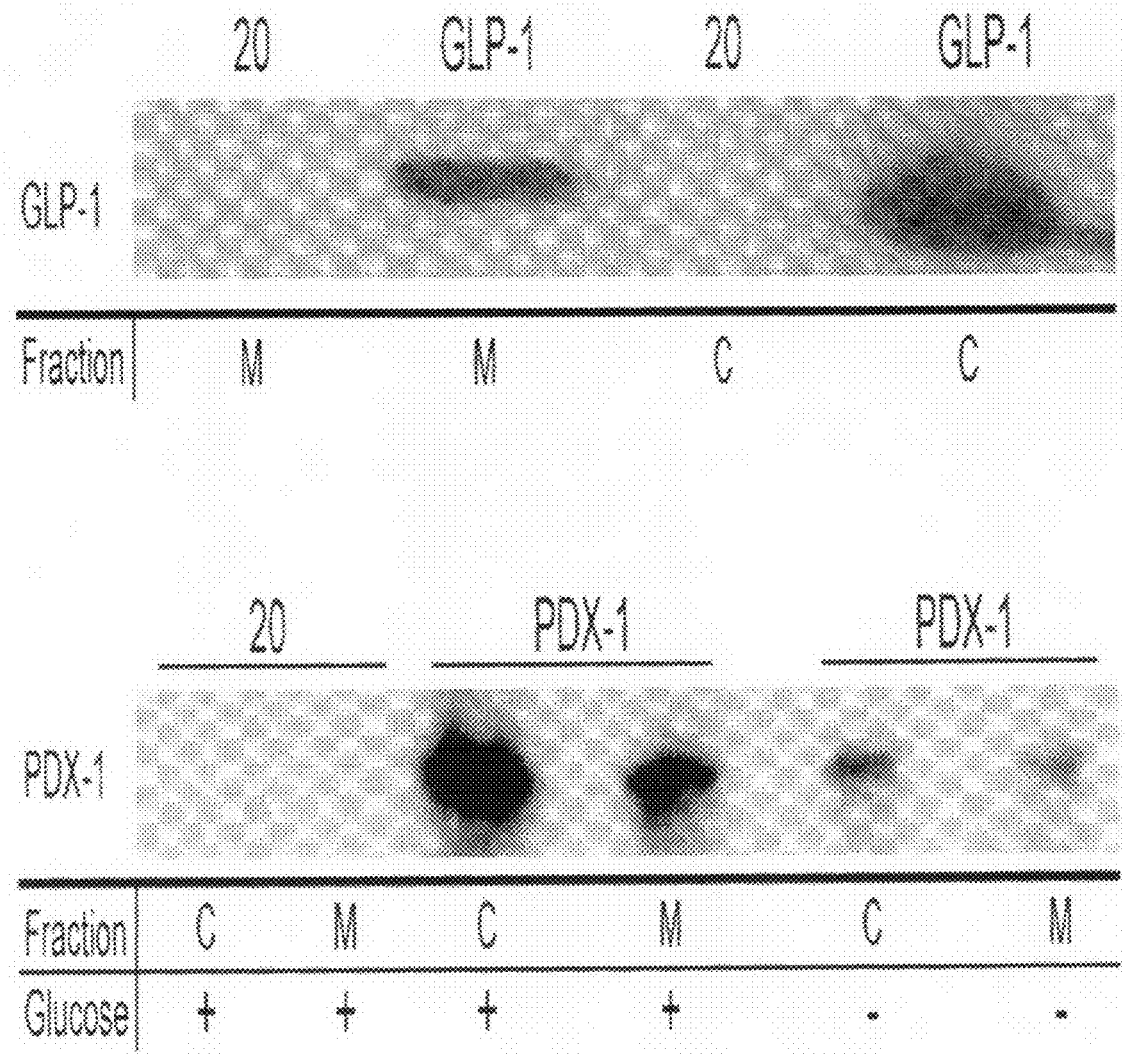

PDX-1 was secreted as a fusion with a cell penetrating peptide (CPP) (Liang, J. F., and V. C. Yang. 2005. Insulin-cell penetrating peptide hybrids with improved intestinal absorption efficiency. Biochemical and Biophysical Research Communications 335:734-738) to facilitate rapid entry into the epithelia post-secretion. Western blots of secreted GLP-1 and PDX-1-CPP in the Nissle supernatant (denoted as fraction "M") and in the Nissle cell pellet (denoted as fraction "C") are shown in FIG. 7. FIG. 7 shows secretion of recombinant insulinotropic proteins from *E. coli* Nissle 1917.

Nissle was engineered to secrete either GLP-1 under control of the fliC promoter or PDX-1-CPP under control of a glucose responsive element. Western blots for secreted proteins GLP-1 (top blot) and PDX-1-CPP (bottom blot) are shown. Cells were grown for 6-8 hours, normalized to an $OD_{600}$=1 and centrifuged. The pellets were lysed and the amount of each protein was determined (fraction "C"). The supernatant was preserved and similarly analyzed (fraction "M"). For cells expressing PDX-1-CPP a comparison was made between cells grown in media containing glucose (0.4%) or glycerol (0.4%). Cells expressing the empty plasmid (denoted as "20") were used as a negative control.

These data showed that both proteins were being secreted. PDX-1 was secreted under control of a glucose-responsive promoter element that had little observed leaky expression (FIG. 7).

To test whether the engineered Nissle strains could induce insulin secretion in human epithelial cells, Caco-2 cells were cultured with cell free media (CFM) from overnight cultures of Nissle strains expressing either PDX-1-CPP, GLP-1, or a 20 amino acid sequence tag (samples denoted as "20") as a negative control. The overnight cultures were grown in F-12K media (Mediatech, Manassas, Va.) without glucose (with the exception of PDX-1 strains which required glucose to produce PDX-1). Culturing of the Caco-2 cells in a 1:1 mix of fresh F-12K media without glucose and CFM from overnights of Nissle secreting PDX-1-CPP, GLP-1, 20, or a combination of half PDX-1-CPP CFM and half GLP-1 CFM ran for 16 hours before the media was removed and the Caco-2 cells were cultured in media with either glucose (0.4%) or glycerol (0.4%) for 2 hours. Following glucose challenge each sample was analyzed for insulin secretion and transcript. As a positive control. Caco-2 cells were incubated in fresh F-12K media (without glucose) and purchased GLP-1 (amino acids 1 through 37, samples denoted as "37") for the same 16 hours time period before being cultured with glucose (0.4%) or glycerol (0.4%) for 2 hours.

A fliC construct (Majander, K., L. Anton, J. Antikainen, H. Lang; M. Brummer, T. K. Korhonen, and B. Westerlund-Wikstrom. 2005. Extracellular secretion of polypeptides using a modified *Escherichia coli* flagellar secretion apparatus. Nature Biotechnology 23:475-481) was used for peptide secretion in *E. coli*.

Figure 8:
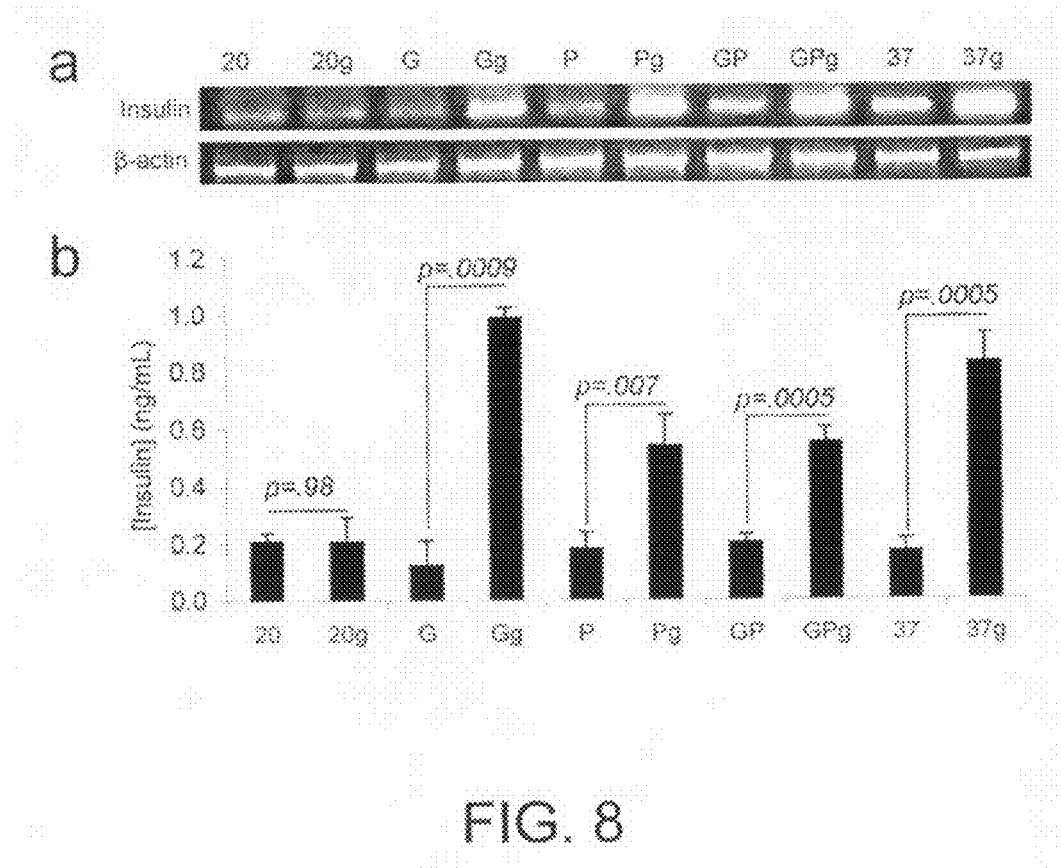

Both transcription and ELISA data indicated that human epithelia incubated with CFM from GLP-1 and PDX-1-CPP either together or separately were stimulated to produce insulin (FIG. 8).

FIG. 8 shows stimulation of insulin secretion in epithelial cells. Caco-2 epithelial cells were incubated with either cell-free media (CFM) from overnight cultures of *E. coli* Nissle 1917 expressing GLP-1 (G), PDX-1-CPP (P), both GLP-1 and PDX-1-CPP (GP), or a control plasmid ("20") or with synthesized GLP-1 (amino acids 1-37, "37") for 6 hours before challenged with glucose or glycerol. a. RT-PCR of Caco-2 cells incubated with CFM from the indicated cell line or protein and subsequent stimulation with either glucose (marked with a small "g") or glycerol. b. ELISA of insulin secretion from stimulated Caco-2 cells. Error bars represent 1 standard deviation of at least triplicate experiments. p values are from a Student's t-test (n=3).

The most insulin production was consistently seen for incubations with GLP-1 CFM or 37. PDX-1-CPP CFM stimulated glucose-responsive insulin secretion whether added by itself or with GLP-1. Both GLP-1- and PDX-1-mediated insulin secretion occurred in response to glucose. The negative control epithelia cultured with CFM from the 20 amino acid sequence tag overnights exhibited no glucose-responsive insulin production (FIG. 8).

That PDX-1-CPP treatment resulted in glucose-responsive insulin secretion in the Caco-2 cells (FIG. 8) was unexpected. Yoshida and coworkers reported that PDX-1 stimulates constitutive insulin production in IEC-6 (rat) epithelia cells, but only when these cells are also treated with betacellulin (Yoshida, S., Y. Kajimoto, T. Yasuda, H. Watada, Y. Fujitani, H. Kosaka, T. Gotow, T. Miyatsuka, Y. Umayahara, Y. Yamasaki, and M. Hori. 2002. PDX-1 induces differentiation of intestinal epithelioid IEC-6 into insulin-producing cells. Diabetes 51:2505-2513). More recent work by Koizumi showing that mice transfected with PDX-1 in vivo expressed insulin from their small intestines, but they did not determine specifically the cells responsible for the secretion and did not determine their glucose responsivity (Koizumi, M., K. Nagai, A. Kida, K. Kami, D. Ito. K. Fujimoto, Y. Kawaguchi, and R. Doi. 2006. Forced expression of PDX-1 induces insulin production in intestinal epithelia. Surgery 140:273-280). The present results imply a distinct difference between human and rat epithelial cells with respect to their response to PDX-1.

It was estimated (calculations and assumptions above) that insulin in the blood would be 164 fmol $L^{-1}$ to 164 pmol $L^{-1}$ for Nissle survivability ranging from $10^6$ to $10^9$ cfu $mL^{-1}$, respectively. Given that postprandial serum insulin concentrations can be as high as 400 pmol $L^{-1}$ for adult non-diabetics (Basu, R., C. Dalla Man, M. Campioni, A. Basu, G. Klee, G. Toffolo, C. Cobelli, and R. A. Rizza. 2006. Effects of age and sex on postprandial glucose metabolism: differences in glucose turnover, insulin secretion, insulin action, and hepatic insulin extraction. Diabetes 55:2001-14), it is encouraging that unoptimized engineered bacteria can stimulate at least within the same order of magnitude insulin release as would be required for normal metabolism.

These results indicate that a promising and easily implemented treatment for type-1 diabetes can be developed based on the above-described methods. With simple oral dosing, no significant background expression and glucose responsiveness, the use of recombinant commensal strains may significantly reduce or even eliminate the need for insulin injection and could help to reduce the long-term complications exhibited by diabetics by replacing host insulin synthesis.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method treating diabetes in a mammalian host comprising:
   administering to the gastrointestinal tract of mammalian host a recombinant enteric commensal bacterium comprising a recombinant nucleic acid molecule encoding a signal that comprises a glucagon-like peptide 1 (Glp-1),
   wherein the signal is expressed by the recombinant enteric commensal bacterium in the gastrointestinal tract and secreted into the gastrointestinal tract of the mammalian host by the recombinant enteric commensal bacterium in the gastrointestinal tract of the mammalian host, and the signal stimulates expression of insulin by the mammalian host to treat said diabetes.

2. The method of claim 1 wherein the commensal bacteria comprises a strain of *Escherichia coli*.

3. The method of claim 2 wherein the strain of *Escherichia coli* comprises *Escherichia coli* Nissle 1917.

4. The method of claim 1 wherein the diabetes is Type I diabetes.

5. A method of treating diabetes in a human, the method comprising:
   administering to the gastrointestinal tract of the human a recombinant enteric commensal bacterium that comprises a recombinant nucleic acid molecule that encodes a signal that comprises glucagon-like peptide 1 (Glp-1),
   wherein the signal is expressed and secreted by the enteric commensal bacterium in the gastrointestinal tract of the human host, and the signal stimulates production of insulin by the human to treat said diabetes.

6. The method of claim 5 wherein the commensal bacteria comprises a strain of *Escherichia coli*.

7. The method of claim 6 wherein the strain of *Escherichia coli* comprises *Escherichia coli* Nissle 1917.

8. The method of claim 5 wherein the diabetes is Type I diabetes.

* * * * *

UNITED STATES PATENT AND TRADEMARK OFFICE
CERTIFICATE OF CORRECTION

| | | |
|---|---|---|
| PATENT NO. | : 8,771,668 B2 | Page 1 of 1 |
| APPLICATION NO. | : 12/937176 | |
| DATED | : July 8, 2014 | |
| INVENTOR(S) | : March et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 364 days.

Signed and Sealed this
Eighth Day of March, 2016

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: tcpA forward primer

<400> SEQUENCE: 1
ggtttggtca gccttggtaa                                              20

<210> SEQ ID NO 2
<211> LENGTH: 20
<212> TYPE: DNA
<213> ORGANISM: Artificial Sequence
<220> FEATURE:
<223> OTHER INFORMATION: tcpA reverse primer

<400> SEQUENCE: 2
tgtgaatgga gcagttcctg                                              20

<210> SEQ ID NO 3
<211> LENGTH: 20
<212> TYPE: DNA
<213> ORGANISM: Artificial Sequence
<220> FEATURE:
<223> OTHER INFORMATION: 16s RNA forward primer

<400> SEQUENCE: 3
cagccacact ggaactgaga                                              20

<210> SEQ ID NO 4
```

```
<211> LENGTH: 20
<212> TYPE: DNA
<213> ORGANISM: Artificial Sequence
<220> FEATURE:
<223> OTHER INFORMATION: 16s RNA reverse primer

<400> SEQUENCE: 4
gttagccggt gcttcttctg                                          20

<210> SEQ ID NO 5
<211> LENGTH: 24
<212> TYPE: DNA
<213> ORGANISM: Artificial Sequence
<220> FEATURE:
<223> OTHER INFORMATION: Human insulin forward primer

<400> SEQUENCE: 5
agcacatcac tgtccttctg ccat                                     24

<210> SEQ ID NO 6
<211> LENGTH: 24
<212> TYPE: DNA
<213> ORGANISM: Artificial Sequence
<220> FEATURE:
<223> OTHER INFORMATION: Human insulin reverse primer

<400> SEQUENCE: 6
ttgttccaca atgccacgct tctg                                     24

<210> SEQ ID NO 7
<211> LENGTH: 32
<212> TYPE: DNA
<213> ORGANISM: Artificial Sequence
<220> FEATURE:
<223> OTHER INFORMATION: Human b-Actin forward primer

<400> SEQUENCE: 7
atctggcacc acaccttcta caatgagctg cg                            32

<210> SEQ ID NO 8
<211> LENGTH: 31
<212> TYPE: DNA
<213> ORGANISM: Artificial Sequence
<220> FEATURE:
<223> OTHER INFORMATION: Human b-Actin reverse primer

<400> SEQUENCE: 8
cgtcatactc ctgcttgctg atccacatct g                             31
```